Figure 1:
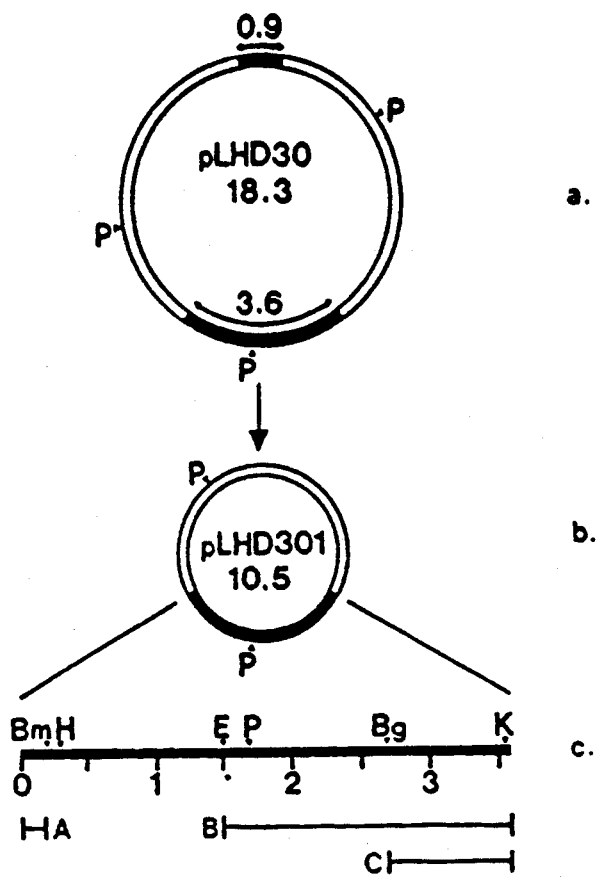

United States Patent [19]

Tubb

[11] Patent Number: 5,028,533
[45] Date of Patent: Jul. 2, 1991

[54] PRECURSOR POLYPEPTIDE, DNA SEQUENCE CODING THEREFOR, VECTORS HOST ORGANISMS, AND PROCESSES INVOLVING SAME

[75] Inventor: Roy S. Tubb, Espoo, Finland

[73] Assignee: CellTech Limited, Berkshire, United Kingdom

[21] Appl. No.: 403,996

[22] PCT Filed: Dec. 23, 1985

[86] PCT No.: PCT/GB85/00599
§ 371 Date: Aug. 20, 1986
§ 102(e) Date: Aug. 20, 1986

[87] PCT Pub. No.: WO86/03778
PCT Pub. Date: Jul. 3, 1986

Related U.S. Application Data

[63] Continuation of Ser. No. 902,414, Aug. 20, 1986, abandoned.

[30] Foreign Application Priority Data

Dec. 21, 1984 [GB] United Kingdom ................ 8432483

[51] Int. Cl.$^5$ .................. C12N 1/16; C12N 15/10; C12N 15/52; C12N 15/79
[52] U.S. Cl. .................. 435/69.1; 435/69.7; 435/69.8; 435/71.1; 435/91; 435/161; 435/171; 435/172.1; 435/172.3; 435/254; 435/320.1; 435/940; 536/27; 935/6; 935/8; 935/9; 935/10; 935/22; 935/28; 935/33; 935/37; 935/47; 935/59; 935/66

[58] Field of Search ............ 435/172.3, 320, 255, 435/161, 252.5, 942, 69.1, 69.7, 69.8, 71.1, 91, 171, 172.1, 172.3, 254, 940; 935/48, 33, 6, 89, 10, 22, 28, 33, 37, 47, 48, 59, 60, 61, 66, 69; 536/27

[56] References Cited

U.S. PATENT DOCUMENTS

| | | | |
|---|---|---|---|
| 4,588,684 | 5/1986 | Brake | 435/68 |
| 4,663,280 | 5/1987 | Sloma | 435/68 |
| 4,663,294 | 5/1987 | Yamane et al. | 435/317 |
| 4,725,535 | 2/1988 | Sonenshein et al. | 435/6 |

FOREIGN PATENT DOCUMENTS 0126206 11/1984 European Pat. Off.

OTHER PUBLICATIONS

Nature, vol. 308, No. 5960, Apr. 12, 1984, S. J. Rothstein et al., pp. 662–665.
Agricultural and Biological Chemistry, vol. 47, No. 11, Nov. 1983.
Brewers' Guardian, Sep. 1984, R. S. Tubb, "Genetic Development of Yeast Strains", pp. 34–37, see page 36.
P. Journal of Bacteriology, vol. 161, No. 2, Feb. 1985, I. Yamashita et al., pp. 567–573, See FIG. 1, Aminoacids 12–32.

Primary Examiner—Richard A. Schwartz
Assistant Examiner—Richard C. Peet
Attorney, Agent, or Firm—Cushman, Darby & Cushman

[57] ABSTRACT

A yeast expression and secretion vector is described. The vector carries a nucleotide sequence coding for a precursor polypeptide which includes the signal sequence of amylo-alpha-1-,-4-glucosidase from *Saccharomyces diastaticus.*

9 Claims, 11 Drawing Sheets

```
  D  L  L  L  P  K  L  N  L  *  K  A  P  Y  Y  S  Y  N  L  L
   I  F  C  F  L  N  *  T  Y  K  K  H  P  I  I  V  I  I  S  C
    S  F  A  S  *  T  K  P  I  K  S  T  L  L  *  L  *  S  L  V
GATGTTTTGCTTCCTAAACTAAACCTATAAAAAGCACCCTATTATAGTTATAATCTCTTGTC
       30        40        50        60        70        80

S  C  C  G  S  N  *  K  Y  T  M  V  G  L  K  N  P  Y  T  H
   H  V  V  V  L  I  E  N  I  L  W  *  A  S  K  I  H  I  R  T
    M  L  W  F  *  L  K  I  Y  Y  G  R  P  Q  K  S  I  Y  A  H
ATGTTGTGGTTCTAATTGAAAATATACTATGGTAGGCCTCAAAAATCCATATACGCAC
       90       100       110       120       130       140

Start
  T  M  Q  R  P  F  L  L  A  Y  L  V  L  S  L  L  F  N  S  A  L
    L  C  K  D  H  F  Y  S  L  I  W  S  F  R  F  Y  L  T  Q  L  W
     Y  A  K  T  I  S  T  R  L  F  G  P  F  A  S  I  *  L  S  F  G
ACTATGCAAAGACCATTTCTACTCGCTTATTTGGTCCTTTCGCTTCTATTTAACTCAGCTTTGGG
       150       160       170       180       190       200

↓
  G  F  P  T  A  L  V  P  R  G  S  S  S  S  N  I  T  S  S
   V  F  Q  L  H  *  F  L  E  D  P  P  L  A  T  S  L  R  P
    F  S  N  C  T  S  S  *  R  I  L  L  *  Q  H  H  F  V  R
TTTTCCAACTGCACTAGTTCCTAGAGGATCCTCCTCTAGCAACATCACTTCGTCC
       210       220       230       240       250       260
                               Bam

G  P  S  S  T  P  F  S  S  A  T  E  S  F  S  T  G  T  T  V  T
   V  H  L  Q  L  H  S  A  L  L  L  K  A  F  L  L  A  L  L  S  L
    S  I  F  N  S  I  Q  L  C  Y  *  K  L  F  Y  W  H  Y  C  H  S
GGTCCATCTTCAACTCCATTCAGCTCTGCTACTGAAAGCTTTTCTACTGGCACTACTGTCACTC
       270       280       290       300       310       320

P  S  S  S  K  Y  P  G  S  K  T  E  T  S  V  S  S  T  T
   H  H  H  P  N  T  L  A  V  K  Q  K  L  L  F  L  L  Q  P
    I  I  I  Q  I  P  W  Q  *  N  R  N  F  C  F  F  Y  N  R
CATCATCATCCAAATACCCTGGCAGTAAAACAGAAACTTCTGTTTCTTCTACAACC
       330       340       350       360       370       380

E  T  T  I  V  P  T  T  T  T  T  S  V  I  T  P  S  T  T  T
   K  L  P  L  F  Q  L  Q  L  R  L  L  S  *  H  H  Q  Q  P  L
    N  Y  H  C  S  N  Y  N  Y  D  F  C  H  N  T  I  N  N  H  Y
GAAACTACCATTGTTCCAACTACAACTACGACTTCTGTCATAACACCATCAACAACCACTA
       390       400       410       420       430       440

I  T  T  T  V  C  S  T  G  T  N  S  A  G  E  T  T  S  G  C
   L  P  L  R  F  A  L  Q  E  Q  T  L  P  V  K  L  L  L  D  A
    Y  H  Y  G  L  L  Y  R  N  K  L  C  R  *  N  Y  F  W  M  L
TTACCACTACGGTTTGCTCTACAGGAACAAACTCTGCCGGTGAAACTACTTCTGGATGC
       450       460       470       480       490       500
```

FIG. 4(i)

```
              S   P   K   T   I   T   T   T   V   P   C   S   T   S   P   S   E   T   A   S   E
          L   Q   R   P   L   Q   L   L   F   H   V   Q   P   V   Q   A   K   P   H   R   N
      S   K   D   H   Y   N   Y   C   S   M   F   N   Q   S   K   R   N   R   I   G   I
TCTCCAAAGACCATTACAACTACTGTTCCATGTTCAACCAGTCCAAGCGAAACCGCATCGGAAT
        510         520         530         540         550         560

S   T   T   T   S   P   T   T   P   V   T   T   V   V   S   T   T   V   V
          Q   Q   P   L   H   L   P   H   L   *   L   Q   L   S   Q   P   P   S   L
      N   N   H   F   T   Y   H   T   C   N   Y   S   C   L   N   H   R   R   Y
CAACAACCACTTCACCTACCACACCTGTAACTACAGTTGTCTCAACCACCGTCGTT
        570         580         590         600         610         620

T   T   E   Y   S   T   S   T   K   Q   G   G   E   I   T   T   T   F   V   T
          L   L   S   I   L   L   V   Q   N   K   V   V   K   L   Q   L   H   L   S   P
      Y   *   V   F   Y   *   Y   K   T   R   W   *   N   Y   N   Y   I   C   H   Q
ACTACTGAGTATTCTACTAGTACAAAACAAGGTGGTGAAATTACAACTACATTTGTCACCA
        630         640         650         660         670         680

K   N   I   P   T   T   Y   L   T   T   I   A   P   T   S   S   V   T   T   V
          K   T   F   Q   P   L   T   *   L   Q   L   L   Q   L   H   Q   S   L   R   L
      K   H   S   N   H   L   P   N   Y   N   C   S   N   F   I   S   H   Y   G   Y
AAAACATTCCAACCACTTACCTAACTACAATTGCTCCAACTTCATCAGTCACTACGGTT
        690         700         710         720         730         740

T   N   E   T   P   T   T   I   T   T   T   V   C   S   T   G   T   N   S   A   G
          P   I   S   P   Q   P   L   L   L   L   R   F   A   L   Q   E   Q   T   L   P   V
      Q   F   H   P   N   H   Y   Y   Y   Y   G   L   L   Y   R   N   K   L   C   R   *
ACCAATTTCACCCCAACCACTATTACTACTACGGTTTGCTCTACAGGAACAAACTCTGCCGGTG
        750         760         770         780         790         800

E   T   T   S   G   C   S   P   K   T   V   T   T   T   V   P   C   S   T
          K   L   P   L   D   A   L   Q   R   L   S   Q   Q   L   F   L   V   Q   L
      N   Y   L   W   M   L   S   K   D   C   H   N   N   C   S   L   F   N   W
AAACTACCTCTGGATGCTCTCCAAAGACTGTCACAACAACTGTTCCTTGTTCAACT
        810         820         830         840         850         860

G   T   G   E   Y   T   T   E   A   T   A   P   V   T   T   A   V   T   T   T
          V   L   A   N   T   L   L   K   L   P   P   L   L   Q   Q   L   S   Q   P   P
      Y   W   R   I   H   Y   *   S   Y   R   P   C   Y   N   S   C   H   N   H   R
GGTACTGGCGAATACACTACTGAAGCTACCGCCCCTGTTACAACAGCTGTCACAACCACCG
        870         880         890         900         910         920

V   V   T   T   E   S   S   T   G   T   N   S   A   G   K   T   T   T   S   Y
          L   L   P   L   N   P   L   R   V   L   T   P   L   V   R   R   Q   L   V   T
      C   Y   H   *   I   L   Y   G   Y   *   L   R   W   *   D   D   N   *   L   H
TTGTTACCACTGAATCCTCTACGGGTACTAACTCCGCTGGTAAGACGACAACTAGTTAC
        930         940         950         960         970         980
```

FIG. 4(ii)

```
        G   D   P   K   W   N   V   D   N   T   A   F   T   E   P   W   G   R   P   Q   N
          E   T   L   S   G   T   S   T   T   R   L   S   R   N   L   G   V   V   L   K   T
            R   P   *   V   E   R   R   Q   H   G   F   H   G   T   L   G   S   S   S   K   R
        GGAGACCCTAAGTGGAACGTCGACAACACGGCTTTCACGGAACCTTGGGGTCGTCCTCAAAACG
            1470      1480Sal   1490      1500      1510      1520

D   G   P   A   L   R   S   I   A   I   L   K   I   I   D   Y   I   K   Q
          M   A   L   L   F   E   A   L   P   S   *   K   S   S   T   T   S   S   N
            W   P   C   S   S   K   H   C   H   L   K   N   H   R   L   H   Q   A   I
        ATGGCCCTGCTCTTCGAAGCATTGCCATCTTAAAAATCATCGACTACATCAAGCAA
            1530      1540      1550      1560      1570      1580

S-  G   T   D   L   G   A   K   Y   P   F   Q   S   T   A   D   I   F   D
          L   A   L   I   W   G   P   S   T   H   S   S   P   P   Q   I   S   L   M
            W   H   *   S   G   G   Q   V   P   I   P   V   H   R   R   Y   L   *   *
        TCTGGCACTGATCTGGGGGCCAAGTACCCATTCCAGTCCACCGCAGATATCTTTGATGAT
            1590      1600      1610      1620      1630      1640

D   I   V   R   W   D   L   R   F   I   I   D   H   W   N   S   S   G   F   D   L
          I   L   Y   V   G   T   *   G   S   L   L   T   T   G   I   L   P   D   L   I   Y
            Y   C   T   L   G   P   E   V   H   Y   *   P   L   E   F   F   R   I   *   S   M
        ATTGTACGTTGGGACCTGAGGTTCATTATTGACCACTGGAATTCTTCCGGATTTGATCTA
            1650      1660      1670      1680      1690      1700

W   E   E   V   N   G   M   H   F   F   T   L   L   V   Q   L   S   A   V   D   R
          G   R   K   S   M   A   C   I   S   L   L   Y   W   Y   N   C   L   Q   W   T   G
            G   G   S   Q   W   H   A   F   L   Y   F   T   G   T   T   V   C   S   G   Q   V
        TGGGAGGAAGTCAATGGCATGCATTTCTTTACTTTACTGGTACAACTGTCTGCAGTGGACAGGT
            1710      1720      1730      1740      1750      1760

S   L   S   Y   F   N   A   S   E   R   S   S   P   F   V   E   E   L   R
          R   C   R   I   L   T   P   Q   N   G   R   L   P   L   L   K   N   C   V
            A   V   V   F   *   R   L   R   T   V   V   S   L   C   *   R   I   A   S
        CGCTGTCGTATTTTAACGCCTCAGAACGGTCGTCTCCCTTTGTTGAAGAATTGCGT
            1770      1780      1790      1800      1810      1820

Q   T   R   R   D   I   S   K   F   L   V   D   P   A   N   G   F   I   N   G   K
          R   H   A   G   T   S   P   S   F   *   W   T   L   R   M   G   L   S   T   A   S
            D   T   P   G   H   L   Q   V   F   S   G   P   C   E   W   V   Y   Q   R   Q   V
        CAGACACGCCGGGACATCTCCAAGTTTTTAGTGGACCCTGCGAATGGGTTTATCAACGGCAAGT
            1830      1840      1850      1860      1870      1880

Y   N   Y   I   V   E   T   P   M   I   A   D   T   L   R   S   G   L   D
          T   I   I   L   L   R   H   P   *   L   P   T   H   *   D   P   D   W   T
            Q   L   Y   C   *   D   T   H   D   C   R   H   I   E   I   R   T   G   H
        ACAATTATATTGTTGAGACACCCATGATTGCCGACACATTGAGATCCGGACTGGAC
            1890      1900      1910      1920      1930      1940
```

FIG. 4 (iv)

```
         I  S  T  L  L  A  A  N  T  V  H  D  A  P  S  A  S  H  L  P  F
       Y  P  L  Y  *  L  R  T  P  S  T  M  R  H  L  L  P  I  F  R  S
         I  H  F  I  S  C  E  H  R  P  R  C  A  I  C  F  P  S  S  V  R
      ATATCCACTTTATTAGCTGCGAACACCGTCCACGATGCGCCATCTGCTTCCCATCTTCCGTTCG
         1950      1960      1970      1980      1990      2000
```

```
         D  I  N  D  P  A  V  L  N  T  L  H  H  L  M  L  H  M  R
       I  S  M  T  L  P  S  *  T  R  C  T  I  *  C  C  T  C  V
         Y  Q  *  P  C  R  P  E  H  V  A  P  F  D  V  A  H  A  F
      ATATCAATGACCCTGCCGTCCTGAACACGTTGCACCATTTGATGTTGCACATGCGT
         2010      2020      2030      2040      2050      2060
```

```
         S  I  Y  P  I  N  D  S  S  K  N  A  T  G  I  A  L  G  R
       R  Y  T  P  S  T  I  A  P  K  M  Q  R  V  L  P  W  A  G
         D  I  P  H  Q  R  *  L  Q  K  C  N  G  Y  C  P  G  P  V
      TCGATATACCCCATCAACGATAGCTCCAAAAATGCAACGGGTATTGCCCTGGGCCGGTAT
         2070      2080      2090      2100      2110      2120
```

```
         Y  P  E  D  V  Y  D  G  Y  G  V  G  E  G  N  P  W  V  L  A  T
       I  L  R  T  Y  M  M  D  M  A  L  A  R  E  I  P  G  S  W  P  R
         S  *  G  R  I  *  W  I  W  R  W  R  G  K  S  L  G  P  G  H  V
      CCTGAGGACGTATATGATGGATATGGCGTTGGCGAGGGAAATCCCTGGGTCCTGGCCACG
         2130      2140      2150      2160      2170      2180
```

```
         C  A  A  S  T  T  L  Y  Q  L  I  Y  R  H  I  S  E  Q  H  D  L
       V  P  L  Q  Q  R  F  I  S  S  F  T  D  T  S  L  S  S  M  T  W
         C  R  F  N  N  A  L  S  A  H  L  Q  T  H  L  *  A  A  *  L  G
      TGTGCCGCTTCAACAACGCTTTATCAGCTCATTTACAGACACATCTCTGAGCAGCATGACTTGG
         2190      2200      2210      2220      2230      2240
```

```
         V  V  P  M  N  N  D  C  S  N  A  F  W  S  E  L  V  F  S
       L  S  Q  *  T  T  I  V  R  T  H  F  G  A  S  W  Y  S  P
         C  P  N  E  Q  R  L  F  E  R  I  L  E  R  A  G  I  L  Q
      TTGTCCCAATGAACAACGATTGTTCGAACGCATTTTGGAGCGAGCTGGTATTCTCC
         2250      2260      2270      2280      2290      2300
```

```
         N  L  T  T  T  L  G  N  D  E  G  Y  L  I  L  E  F  N  T  P  A
       T  S  R  L  W  E  M  T  K  A  I  *  F  W  S  S  I  H  L  P
         P  H  D  F  G  K  *  R  R  L  F  D  F  G  V  Q  Y  T  C  L
      AACCTCACGACTTTGGGAAATGACGAAGGCTATTTGATTTTGGAGTTCAATACACCTGCCT
         2310      2320      2330      2340      2350      2360
```

```
         F  N  Q  T  I  Q  K  I  F  Q  L  A  D  S  F  L  V  K  L  K
       S  I  K  P  Y  K  K  S  S  N  *  L  I  H  S  W  S  S  *  K
         Q  S  N  H  T  K  N  L  P  T  S  *  F  I  L  G  Q  A  E  S
      TCAATCAAACCATACAAAAAATCTTCCAACTAGCTGATTCATTCTTGGTCAAGCTGAAA
         2370      2380      2390      2400      2410      2420
```

FIG. 4(v)

FIG. 5 (i)

```
                                                              M   W   L   L
AGAGAAACAGAATCCTAACTATTTCTGAGGAAACTGCAGGTCCAAAATGTGGCTGCTTTT
         10        20        30        40        50        60

-1  +1
                                                 | L   F   G   K   L   -
   T   M   A   S   L   I   S   V   L   G   T   T   H   G | L   F   G   K   L   H
AACAATGGCAAGTTTGATATCTGTACTGGGGACTACACATGG|TTGTTTGGAAAATTACA
         70        80        90       100       |   110       120

P   -   S   P   E   V   T   M   -   I   S   Q   M   I   T   Y   W   -   Y   -   N
   P   G   S   P   E   V   T   M   N   I   S   Q   M   I   T   Y   W   G   Y   P   N
TCCTGGAAGCCCTGAAGTGACTATGAACATTAGTCAGATGATTACTTATTGGGGATACCCAAA
        130       140       150       160       170       180

E   E   Y   E   V   V   T   E   D   G   Y   I   L   E   V   N   R   I   P
TGAAGAATATGAAGTTGTGACTGAAGATGGTTATATTCTTGAAGTCAATAGAATTCC
        190       200       210       220       230       240

Y   G   K   K   N   S   G   N   T   G   Q   R   P   V   V   F   L   Q   H   G
TTATGGGAAGAAAAAATTCAGGGAATACAGGCCAGAGACCTGTTGTGTTTTTGCAGCATGG
        250       260       270       280       290       300

L   L   A   S   A   T   N   W   I   S   N   L   P   N   N   S   L   A   F   I
TTTGCTTGCATCAGCCACAAACTGGATTTCCAACCTGCCGAACAACAGCCTTGCCTTCAT
        310       320       330       340       350       360

L   A   D   A   G   Y   D   V   W   L   G   N   S   R   G   N   T   W   A   R
TCTGGCAGATGCTGGTTATGATGTGTGGCTGGGCAACAGCAGAGGAAACACCTGGGCCAG
        370       380       390       400       410       420

R   N   L   Y   Y   S   P   D   S   V   E   F   W   A   F   S   F   D   E   M
AAGAAACTTGTACTATTCACCAGATTCAGTTGAATTCTGGGCTTTCAGCTTTGATGAAAT
        430       440       450       460       470       480

A   K   Y   D   L   P   A   T   I   D   F   I   V   K   K   T   G   Q   K   Q
GGCTAAATATGACCTTCCAGCCACAATCGACTTCATTGTAAAGAAAACTGGACAGAAGCA
        490       500       510       520       530       540

L   H   Y   V   G   H   S   Q   G   T   T   I   G   F   I   A   F   S   T   N
GCTACACTATGTTGGCCATTCCCAGGGCACCACCATTGGTTTTATTGCCTTTTCCACCAA
        550       560       570       580       590       600

P   S   L   A   K   R   I   K   T   F   Y   A   L   A   P   V   A   T   V   K
TCCCAGCCTGGCTAAAAGAATCAAAACCTTCTATGCTCTAGCTCCTGTTGCCACTGTGAA
        610       620       630       640       650       660

Y   T   K   S   L   I   N   K   L   R   F   V   P   Q   S   L   F   K   F   I
GTATACAAAAAGCCTTATAAACAAACTTAGATTTGTTCCTCAATCCCTCTTCAAGTTTAT
        670       680       690       700       710       720
```

```
           F   G   D   K   I   F   Y   P   H   N   F   F   D   Q   F   L   A   T   E   V
       ATTTGGTGACAAAATATTCTACCCACACAACTTCTTTGATCAATTTCTTGCTACTGAAGT
            730         740         750         760         770         780

C   S   R   E   M   L   N   L   L   C   S   N   A   L   F   I   I   C   G   F
       GTGCTCCCGTGAGATGCTGAATCTCCTTTGCAGCAATGCCTTATTTATAATTTGTGGATT
            790         800         810         820          830         840

D   S   K   N   F   N   T   S   R   L   D   V   Y   L   S   H   N   P   A   G
       TGACAGTAAGAACTTTAACACGAGTCGCTTGGATGTGTATCTATCACATAATCCAGCAGG
            850         860         870         880         890         900

T   S   V   Q   N   M   F   H   W   T   Q   A   V   K   S   G   K   F   Q   A
       AACTTCTGTTCAAAACATGTTCCATTGGACCCAGGCTGTTAAGTCTGGGAAATTCCAAGC
            910         920         930         940         950         960

Y   D   W   G   S   P   V   Q   N   R   M   H   Y   D   Q   S   Q   P   P   Y
       TTATGACTGGGGAAGCCCAGTTCAGAATAGGATGCACTATGATCAGTCCCAACCTCCCTA
            970         980         990        1000        1010        1020

Y   N   V   T   A   M   N   V   P   I   A   V   W   N   G   G   K   D   L   L
       CTACAATGTGACAGCCATGAATGTACCAATTGCAGTGTGGAACGGTGGCAAGGACCTGTT
           1030        1040        1050        1060        1070        1080

A   D   P   Q   D   V   G   L   L   L   P   K   L   P   N   L   I   Y   H   K
       GGCTGACCCCCAAGATGTTGGCCTTTTGCTTCCAAAACTCCCCAATCTTATTTACCACAA
           1090        1100        1110        1120        1130        1140

E   I   P   F   Y   N   H   L   D   F   I   W   A   M   D   A   P   Q   E   V
       GGAGATTCCTTTTTACAATCACTTGGACTTTATCTGGGCAATGGATGCCCCTCAAGAAGT
           1150        1160        1170        1180        1190        1200

Y   N   D   I   V   S   M   I   S   E   D   K   K   *
       TTACAATGACATTGTTTCTATGATATCAGAAGATAAAAAGTAGTTCTGGATTTAAAGAAT
           1210        1220        1230        1240        1250        1260

TATCCGTTTGTTTTTCCAAAATACTTTATTCTCTCATACATAGTATTTTCATAATGTTTG
           1270        1280        1290        1300        1310        1320

ACATGCAGTGCTTCTTTCTGTAATTTTGACTTTAGAAATATATTGGC
           1330        1340        1350        1360     1
```

FIG. 5(ii)

PRECURSOR POLYPEPTIDE, DNA SEQUENCE CODING THEREFOR, VECTORS HOST ORGANISMS, AND PROCESSES INVOLVING SAME

This is a continuation of application Ser. No. 06,902,414, filed Aug. 20, 1986 which was abandoned upon the filing thereof.

FIELD OF THE INVENTION

This invention relates to the field of recombinant DNA biotechnology.

BACKGROUND OF THE INVENTION

It has been suggested that starch (or dextrin)-degrading yeasts could be usefully exploited in fermentation processes, such as the production of ethanol or beer, which utilise starch-containing raw materials (Tubb, 1983, 1984: full reference to be found at the end of this specification), and in the production of amylolytic enzymes such as amyloglucosidases (Eveleigh, 1981; Fogarty, 1983). Dex+ strains of *Saccharomyces cerevisiae* (formerly called *S. diastaticus;* van der Walt, 1970; Yarrow, 1984) have at least one DEX or STA gene (Erratt and Stewart, 1978; Tamaki, 1978) and are able to ferment soluble starch or dextrins as a consequence of producing an extracellular amylo-α-1,4-glucosidase (AMG) during vegetative growth (Hopkins, 1955; Searle and Tubb, 1981). However, common brewing strains of *Saccharomyces cerevisiae* do not have the ability to produce extracellular AMG during vegetative growth. Dex+ strains of *Saccharomyces cerevisiae* have been hybridised with brewing strains, and progeny have been derived which have the ability to produce AMG during vegetative growth. However these progeny strains produce unacceptable low carbohydrate beers (Tubb et al., 1981), unless steps are taken to eliminate a gene (POF1) responsible for a 'herbal phenolic' off-flavor (Goodey and Tubb, 1982).

Recombinant DNA techniques offer a more specific approach to conferring amylolytic character on strains of yeast already possessing many other desirable commercial characteristics. Recently, α-amylase genes from mice (Thomsen, 1983) and wheat (Rothstein et al., 1984) have been expressed in *S. cerevisiae,* and a gene for AMG production has been cloned from a STA1 strain of yeast (Yamashita and Fukui, 1983).

A 3.6kb DNA fragment has been cloned from a *Saccharomyces diastaticus* genome (strain BRG536): DEX1) and shown to confer production of extracellular amylo-α-1,4-glucosidase (AMG), and thereby, the ability to hydrolyse starch and dextrins, on Dex− strains of *S. cerevisiae* (Tubb, R. S., Brewers Guardian, Sept. 1984, 34–37). (A preliminary report of this work was given at the ALKO Symposium on gene expression in yeast at Helsinki in June, 1983).

The use of a eukaryotic signal sequence to promote product transport from a eukaryotic host cell harbouring a recombinant vector is known. Published European patent application EP-A1-0127304 describes fusion polypeptides comprising a signal (or "pre") sequence and a desired polypeptide produced by expression of a gene in a host cell. The fusion polypeptides are transported through the host cell membrane and cleaved to produce extracellular, mature, polypeptides. The yeast invertase signal sequence is specifically mentioned and its use in the preparation of host cells capable of producing extracellular interferon is described. Published European patent application EP-A1-0116201 describes an essentially similar use of eukaryotic signal sequences and exemplifies the use of the yeast α-factor signal sequence in the production of extracellular human epidermal growth factor (hEGF). The existence and use of the signal sequence of a yeast amylolytic enzyme to promote product secretion of heterologous polypeptides from yeast has been the subject of speculation (Tubb, R. S., Brewers Guardian, Sept. 1984, 34–37).

The cloned 3.6kb DNA fragment referred to above has now been sequenced and the coding sequence for AMG has been identified and elucidated. In addition, it has been unequivocally shown that the AMG gene includes a leader sequence coding for a signal peptide capable of promoting product secretion.

According to the present invention, there is provided a precursor polypeptide having the amino acid sequence:

met-gln-arg-pro-phe-leu-leu-ala-tyr-leu-val-leu-ser-leu-leu-phe-asn-ser-ala-leu-gly-X wherein X is a polypeptide.

The precursor polypeptide, when produced in a eukaryotic host cell by the expression of a gene coding for the precursor polypeptide, is exported from the host cell and processed to produce the mature polypeptide, X.

The polypeptide X may be any polypeptide such as an enzyme, a hormone, a lymphokine or the like. The mature polypeptide may itself be a precursor such as a pro form. Particular examples described herein are the yeast enzyme AMG, the mammalian enzyme, gastric lipase and the mammalian lymphokine, interferon-α 2. The amino acid sequences for the AMG and human gastric lipase are shown in FIGS. 4 and 5 respectively.

In a further aspect of the invention there is provided a DNA sequence coding for a precursor polypeptide according to the invention. The DNA sequence may be used to construct vectors for use in transforming eukaryotic host cells. The DNA sequence may have the following nucleotide sequence:

5'-ATGCAAGACCATTTCTACTCGCT-
TATTTGGTCCTTTCGCTTCTATTTAACT-
CAGCTTTGGGT(X¹)-3' wherein $X^1$ is the coding sequence of the polypeptide X.

In a further aspect of the invention, there is provided a eukaryotic expression vector including a DNA sequence of the invention positioned relative to a promoter capable of directing expression of the DNA sequence when the vector is transformed into a eukaryotic host cell, provided that when the polypeptide X is amylo-α-1,4-glucosidase, the promoter is not an amylo-α-1,4-glucosidase gene promoter.

The promoter may be any functionally active eukaryotic promoter but is preferably a yeast promoter, such as a promoter derived from the phosphoglycerate kinase (PGK) gene. The vector is adapted for expression in a eukaryotic host cell by the provision of selectable markers and control regions as, appropriate.

In a further aspect of the invention there is provided a eukaryotic host organism transformed with a vector of the invention. The host organism may be any eukaryotic organism including mammalian cells in tissue culture, but is preferably a yeast. Especially preferred are strains of *Saccharomyces cerevisiae.* Where the polypeptide X is an amlolytic enzyme, the yeast is preferably a brewing strain.

In a further aspect of the invention there is provided a fermentation process for producing ethanol comprising the step of culturing a yeast, in the presence of starch or dextrin, transformed with a vector of the invention including a gene coding for an amylolytic enzyme.

Such a fermentation will allow for the super-attenuation of wort liquor and consequently the production of a low-carbohydrate beer.

In a further aspect of the invention there is provided a process for the production of a polypeptide comprising growing, in a culture medium, a eukaryotic host organism transformed with a vector of the invention and isolating the polypeptide from the culture medium.

Figure 3:
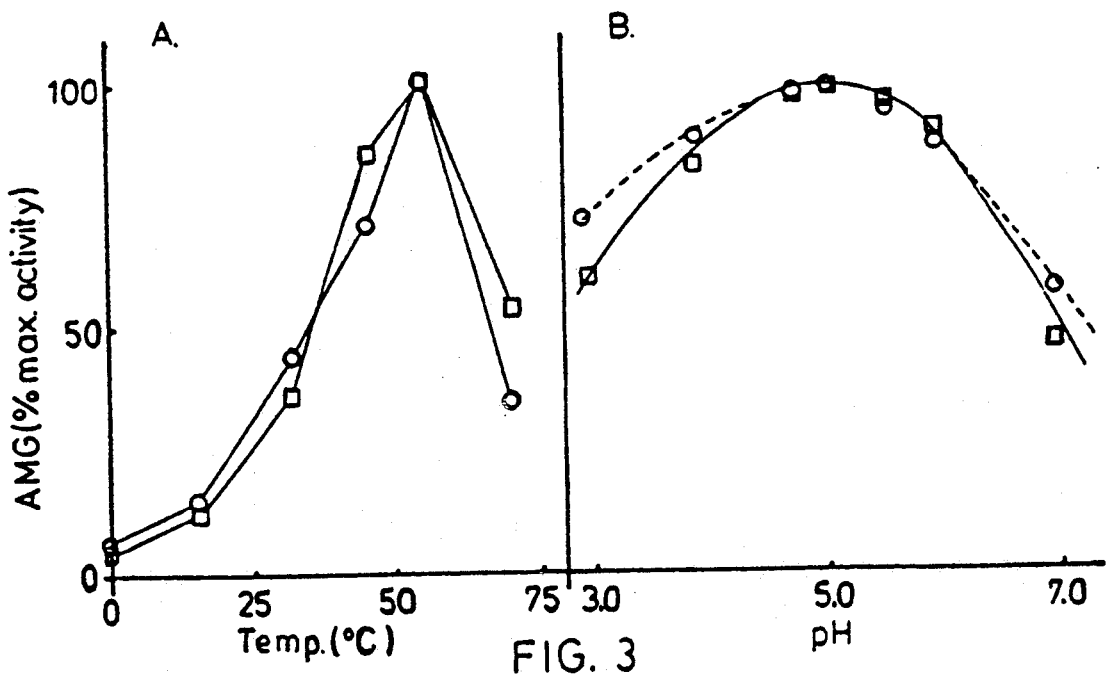
Figure 2:
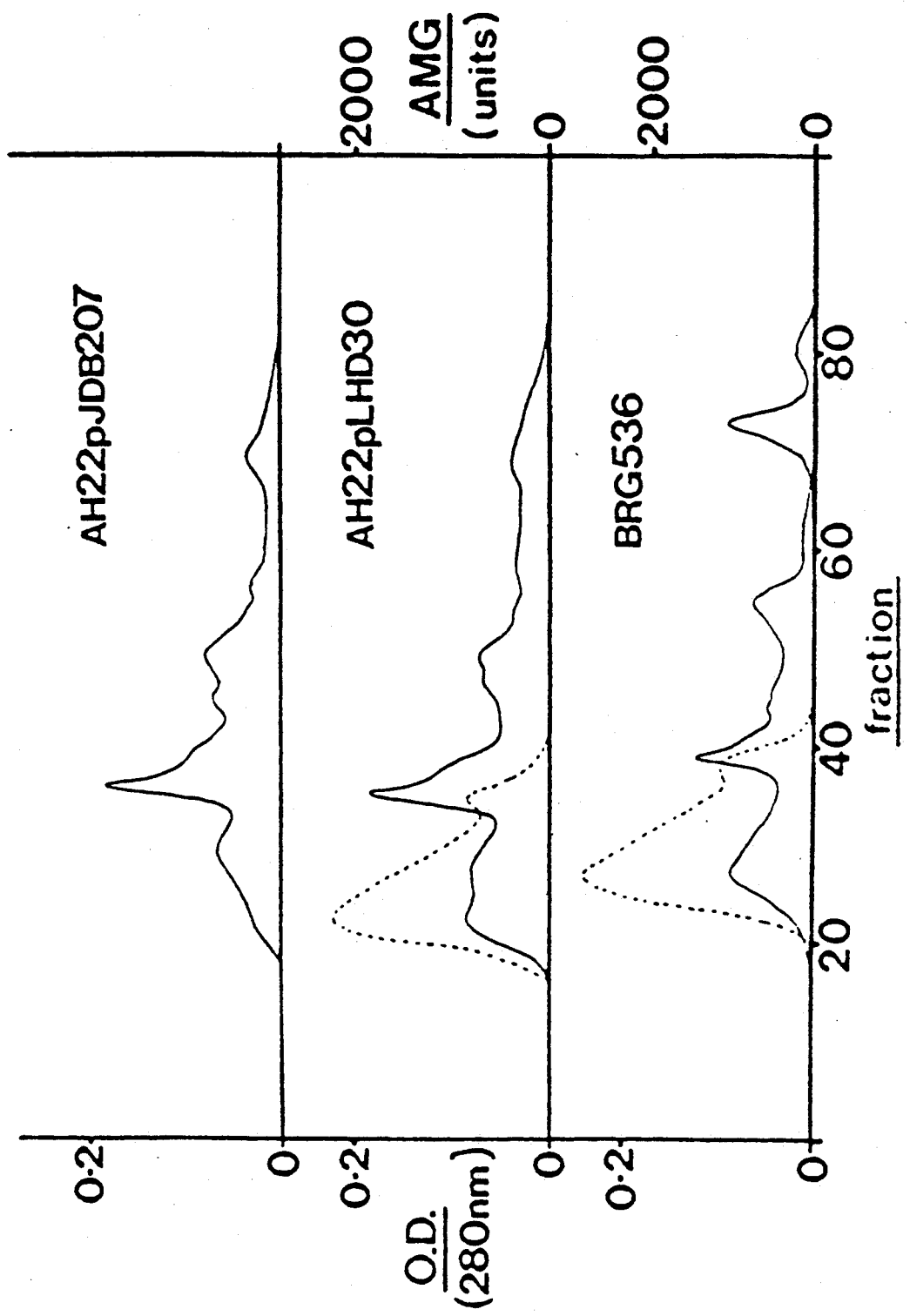

The invention is now described with reference to the following Examples which refer to the accompanying drawings in which:

FIG. 1 shows plasmid and restriction maps of plasmids pLHD30 and pLHD301,

FIG. 2 shows a comparison between strains of extracellular proteins after elution from DEAE-Sepharose, FIG. 3 shows the effect of temperature (FIG. 3a) and pH (FIG. 3b) on the activity of AMG from BRG 536(O) and from AH22[pLAD30](□), FIG. 4 shows the complete DNA and amino acid sequence of the AMG precursor, The reading frame for the AMG amino acid sequence is the top-most of the three reading frames commencing, for the AMG precursor polypeptide, with the methionine residue (M) corresponding to the ATG codon at nucleotides 144-146 and ending with the TAG stop codon at nucleotides 2562-2564. The mature AMG amino acid sequence commences with the phenylalanine residue (F) corresponding to the TTT codon at nucleotides 207-209.

Figure 6:
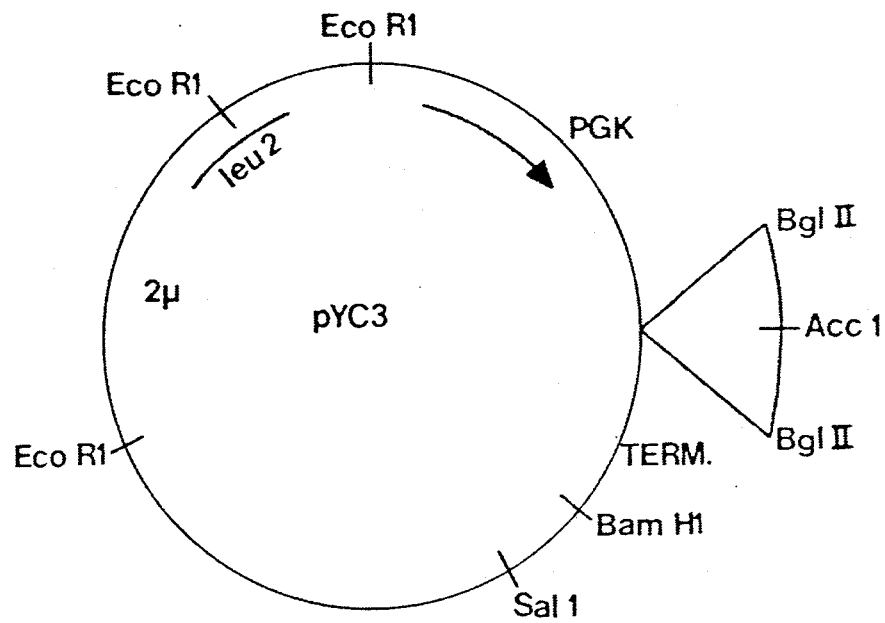
Figure 8:
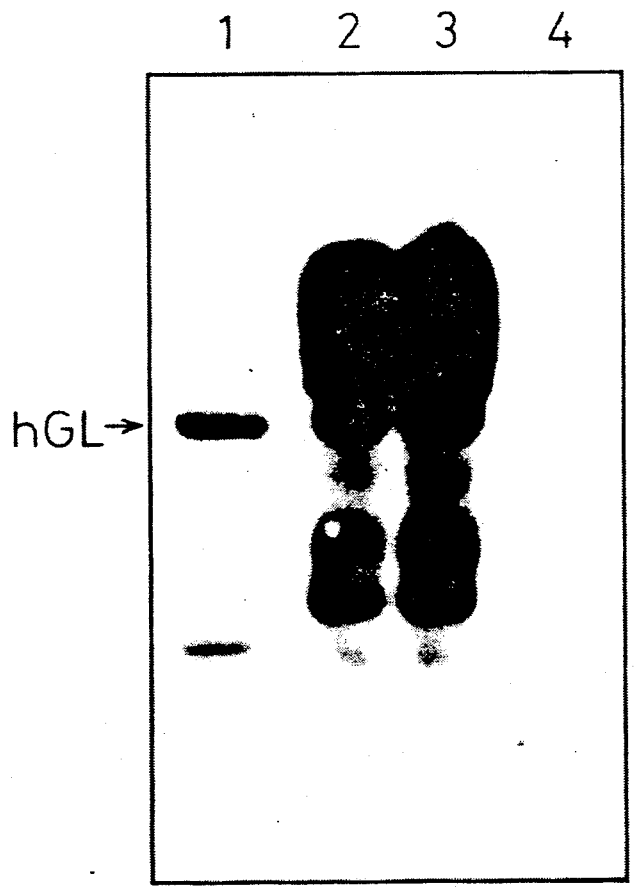
Figure 9:
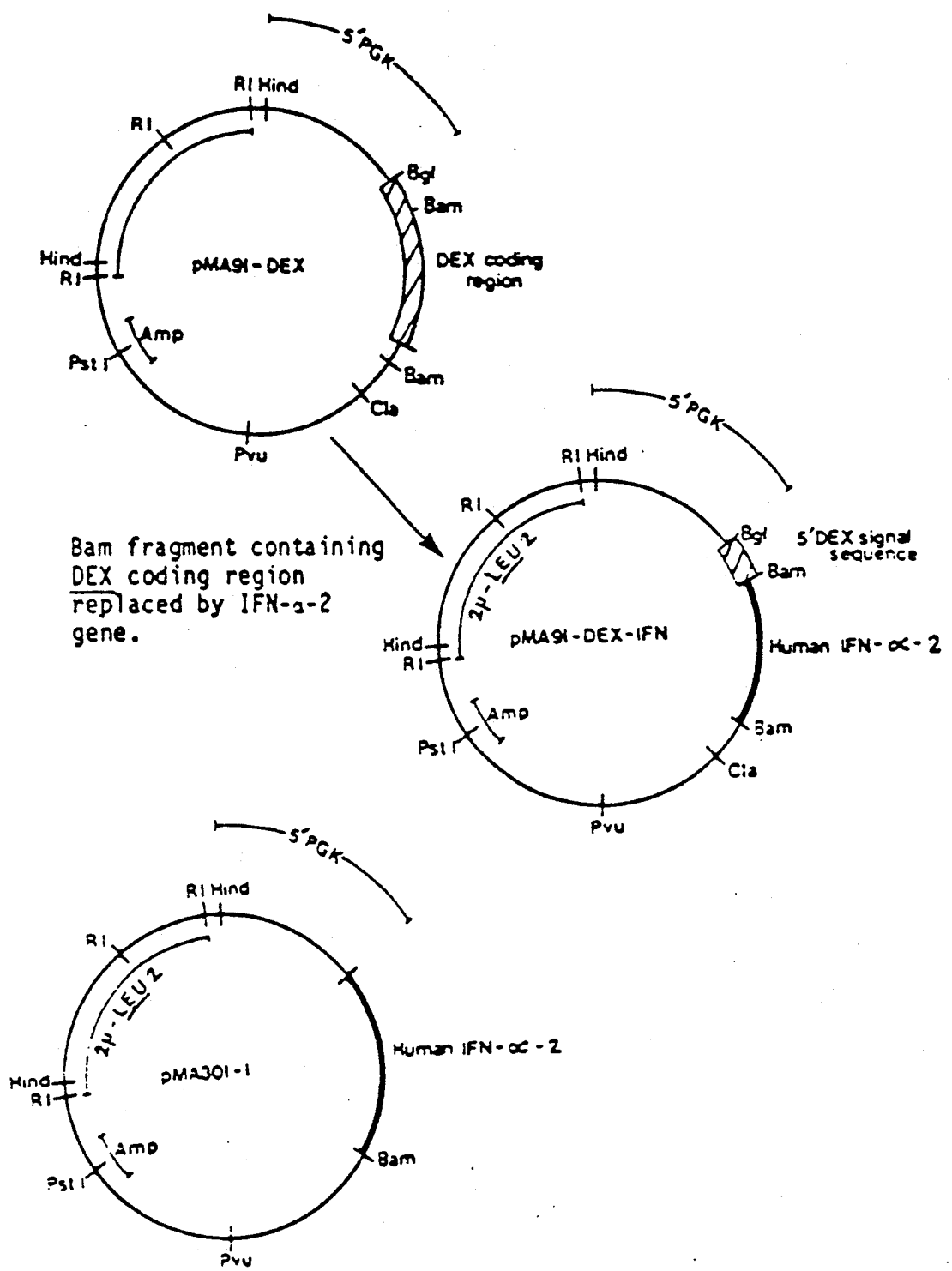

FIG. 5 shows the complete DNA and amino acid sequence of human pregastric lipase, FIG. 6 shows a restriction map of plasmid pYC3, FIG. 7 a photograph (7(a)) and an autoradiogram (7(b)) at an agar plate, including colonies of HGL secreting transformed yeast hosts, FIG. 8 shows a Western blot polyacrylamide gel of the protein products of a transformed yeast, and FIG. 9 shows a restriction map of plasmids pMA91-DEX, pMA301-1 and pMA91-DEX-IFN.

In the DNA sequence of FIGS. 4 and 5 and elsewhere in the present description:

G—denotes a guanosine nucleotide residue
T—denotes a thymidine nucleotide residue
A—denotes a adenosine nucleotide residue, and
C—denotes a cytosine nucleotide residue In the amino acid sequences of FIGS. 4 and 5 and elsewhere in the present description:

A—denotes an alanine residue
C—denotes a cysteine residue
D—denotes an aspartic acid residue
H—denotes a histidine residue
E—denotes an glutamic acid residue
F—denotes a phenylalanine residue
G—denotes a glycine residue
H—denotes a histidine residue
I—denotes an isoleucine residue
K—denotes a lysine residue
L—denotes a leucine residue
M—denotes a methionine residue
N—denotes an asparagine residue
P—denotes a proline residue
Q—denotes a glutamine residue
R—denotes an arganine residue
S—denotes a serine residue
T—denotes a threonine residue
V—denotes a valine residue
W—denotes a tryptophan residue, and
Y—denotes a tyrosine residue

EXAMPLE 1

Materials and Methods

1) Strains and Plasmids

The yeast strains used are listed in Table 1 below. *Escherichia coli* DH1 (F−recA1 endA1 gyrA96 thi-1 hsdR17 supE44), was used for the propagation and amplification of plasmid DNA. The yeast-*E. coli* vector was that denoted pJDB207 (Beggs, 1981).

TABLE 1

| Strain | Known genotype[a] | Origin or derivation |
|---|---|---|
| X4003-5B | a leu2 ade1 his4 met2 ura3 gal1 cdx1 | Genetic Stock Center Berkeley |
| AH22 | a leu2 his4 CDX1 | Hinnen et al (1978) |
| BRG536 | α DEX1 cdx1 | Goodey and Tubb (1982) |
| BRG136B | a lys2 DEX1 CDX1 | b |
| BRG205B | a ade1 DEX1 CDX1 | c |
| BRG136D | a dex1 | b |
| BRG139A | a dex1 | b |
| BRG140A | a dex1 | b |

[a]Since a Cdx+ or Cdx− phenotype can only be observed in Dex+ strains, the genotype of Dex− strains (X4003-5B and AH22) were deduced by analysis of the meiotic progeny from crosses with DEX1 CDX1 strains.
[b]Derived from a cross between BRG536 and SA (Goodey and Bevan, 1983)
[c]Derived from a cross between BRG536 and CB1J (ten Berge et al, 1973).

2) Yeast Growth Media

The medium denoted 'YPG' contained 20 g glucose, 10 g yeast extract and 10 g bacto-peptone per liter. In the medium denoted 'YP5G', the glucose concentration was increased to 50 g $1^{-1}$. The medium denoted 'GYNB' contained 20 g glucose and 6.7 g Yeast Nitrogen Base ('YNB'; Difco) per liter. In the medium denoted 'SGYNB', the glucose concentration was increased to 30 g $1^{-1}$ and the medium (pH 5.4) was buffered with 0.05 M citrate (12.7 mM citric acid, 37.3 mM sodium citrate). The medium denoted 'DEXYNB' contained dextrin (Sigma, Type IV; 20 g $1^{-1}$) instead of glucose. Auxotrophic requirements were met by additional supplements (100 μg ml$^{-1}$) where necessary. In order to impose a selection for maintenance of plasmids, Leu[30] transformants growing in YNB media were not provided with leucine. Where required, media were solidified with agar (20 g $1^{-1}$). Sorbitol (1.2 M) was incorporated as osmotic stabiliser when regenerating transformants.

3) Isolation, Restriction, Ligation and Analysis of DNA

Plasmid DNA was prepared from yeast by the method of Brown et al. (1981). Total DNA was prepared in the same way, but the centrifugation step immediately following cell lysis was omitted. DNA for cloning was purified further by caesium chloride (CsCl) density gradient centrifugation.

Bulk and mini-scale preparations of plasmid DNA from *E. coli* were performed by alkaline lysis (Maniatis et al. 1982). Horizontal gel electrophoresis was carried out as described by Brown et al. (1981).

Restriction enzymes BamHI, EcoRI, HindIII and PstI, were purchased from Boehringer-Mannheim, BglII and KpnI from P+S Biochemicals, and Sau3A from Bethesda Research Laboratories. T4 DNA ligase was from New England Biolabs. Enzyme reactions (digestions and ligations) were carried out in accordance with the suppliers' instructions. For cloning experiments, linearised vector DNA was treated with alkaline phosphatase from calf intestine (Boehringer-Mannheim; Bolivar and Backman, 1979) prior to ligation with genomic fragments.

4) Transformation Procedures

Yeast transformation was carried out using the procedure of Beggs (1978) except that double the concentration of plasmid DNA was used. Transformation of *E. coli* DH1 was performed following the method of Maniatis et al. (1982) for *E. coli* X1776.

5) Southern Transfers and Hybridisations

Radiolabelled DNA was prepared from $^{32}$P-labelled dCTP (Amersham International) using a nick translation kit (Bethesda Research Laboratories) in accordance with the manufacturer's instructions. Transfers and hybridisations (Southern, 1975) were carried out with Biodyne A nylon membranes (Pall Process Filtration Ltd.) using protocols provided by the manufacturer. Autoradiography was performed at room temperature using Fuji RX film with intensification.

6) Other Genetic Techniques

Mating, sporulation of diploids, analysis of meiotic progeny and other general genetic procedures were essentially as described by Sherman and Lawrence (1974). A Dex$^+$ phenotype was scored as growth on DEXYNE agar and confirmed by testing cells or culture supernatants (prepared as described in (7) below) for the presence of AMG by the rapid method of Searle and Tubb (1981).

7) AMG Activity Measurements

In examining the regulation of AMG production and the location of AMG activity, inocula were prepared by growing strains for 48 h at 25° C. in GYNB and then in YP5G for a further 24 h. Conditions of glucose excess were maintained by subculturing into YP5G (10 to 30 μl into 10 ml). Glucose-limited growth was established by using YP medium (100 ml) and a diffusion capsule (LH Engineering) containing 1 ml glucose solution (50%, w/v). When growing transformants, loss of plasmid was monitored by plating out culture samples for single colonies on GYNB+leucine, replica plating to GYNB (without leucine) and determining the proportion of Leu$^-$ colonies.

Culture supernants for assay were recovered by centrifugation. To prepare a cell homogenate, the yeast pellet was washed twice and suspended in its own weight of citrate-phosphate buffer (48.5 mM sodium citrate, 103 mM Na$_2$HPO$_4$, pH5). Cells were disrupted with glass beads in a Braun homogeniser cooled with liquid CO$_2$ and the cell homogenate was decanted from the glass beads. To prepare protoplasts, yeast cells were suspended in 0.86 M mercaptoethanol, 1.2 M sorbitol, 25 mM EDTA, pH8, for 20 minutes at 30° C., and then for 90 minutes in 1.2 M sorbitol, 0.1 M sodium citrate, 10 mM EDTA, pH5.8 (5 ml), containing Zymolyase 60,000 (Miles Laboratories; 4 mg ml$^{-1}$). The complete removal of cell wall material was checked in each case by microscopic examination. After three washes in the same buffer, protoplasts were lysed by the addition of water.

For assay, culture supernants were membrane filtered, dialysed at 4° C. again citrate-phosphate buffer (pH5; 4×2 liters) and diluted 1:1 with the same buffer containing maltotriose (2%, w/v). Cell homogenates and protoplast lysates were diluted with water as necessary and assayed similarly at pH5 against maltotriose (1%, w/v) as substrate. Reactions in screw-capped tubes at 25° C. were terminated by immersion in boiling water, membrane filtered where necessary (assays of cell homogenates or protoplast lysates), and the glucose released by AMG from maltotriose measured by an enzyme-linked colorimetric procedure (Glucoquant Test Kit; Boehringer). In the samples analysed, α-gluocosidase (maltase) activity (assayed using p-nitrophenyl-α-D-glucoside as substrate) was insignificant; therefore, deactivation of this activity by subjecting protoplast lysates and cell homogenates to 55° C. (Searle, 1982) was omitted. Enzyme activity of cultures was related to cell dry weight which was determined by a standard procedure (Anon, 1977).

To examine the effect of pH on activity of purified enzyme, samples in citrate-phosphate buffer (pH5) were dialysed against deionised water to remove salts and diluted with buffer containing maltotriose. Buffers with pH values in the range 3.0 to 7.0 were constructed by mixing the required volumes of 0.05 M sodium citrate and 0.1 M Na$_2$HPO$_4$. To determine the effects of temperature on AMG activity, samples in citrate-phosphate, pH5, were held at temperatures in the range 0° to 70° C. for 1 hour, cooled and assayed against maltotriose.

8) Analysis of Extracellular Proteins and Purification of AMG

Yeast strains were propagated aerobically in SGYNB and subcultured into the same medium (2 liters) using an inoculum of 2.5 [g. wet wt.]1$^{-1}$. Cultures were stirred (160 rev. min$^{-1}$) under air for 3d at 25° C. Culture supernatants were recovered by centrifugation, clarified by filtration (0.45 μm; Millipore), and concentrated to between 10 and 20 ml by ultrafiltration through a Diaflo PM30 membrane (Amicon). After overnight dialysis against 4×2 liters phosphate buffer (0.5 M; pH7.0) concentrates were made 4 M with respect to urea and passed through a DEAE-Sepharose CL-6B ion-exchange column (Pharmacia) equilibrated with phosphate buffer. Elution was with a 0 to 1 M NaCl gradient in the same buffer, monitoring absorbance continuously at 280 nm and collecting 4 ml fractions. Fractions were assayed for protein (Lowry et al. 1951) and AMG activity (see (7) above).

Protein preparations were examined by SDS-PAGE using the method of Laemmli (1970). Gels were loaded with between 10 and 50 μg protein per channel and after electrophoresis, were stained for protein using Coomassie Blue R250 of, for carbohydrate, using Fuchsin-sulphate (Zacharius et al., 1969).

For further purification, fractions possessing AMG activity after ion-exchange chromatography were pooled, concentrated with Aquacide IIA (Calbiochem), diluted in a small volume of 0.05 M imidazone-HCl buffer (pH7.4) containing 4 M urea, and applied to a chromatofocussing column containing Polybuffer Exchanger PBE 94 (Pharmacia). Elution was with polybuffer 74 (Pharmacia) over the range pH7 to pH4. Fractions containing AMG were again pooled, concentrated with Aquacide, diluted with citrate-phosphate buffer, pH5 (1 to 2 ml) and, using the same buffer for elution, subjected to chromatography through a Biogel P150 (Bio Rad) gel-permeation column. This final purification step also served to remove the ampholytes used in chromatofocussing.

9) DNA Sequence Determination

The nucleotide sequence of the cloned 3.6 Kb fragment was determined by the dideoxy method (Sanger et al., (1977) after subcloning restriction fragments from pLHD301 (see below) into M13 mp9 or mp10 (Amersham) and transformation into JM101 (Messing and Vieira (1982).

10) Protein Sequence Determination

Mature AMG protein was produced by S. cerevisiae transformed with a PGK-based plasmid (pMA91 - see published European Patent Application EPO No. 073635) containing a gene for AMG derived from pLHD301 (see below). Protein was purified as described above in (8) and terminal amino acid sequence was determined by automated Edman degradation using a gas phase sequenator.

Results a) Cloning of a DEX gene

Total DNA (50 μg) prepared from S. cerevisiae strain BRG536 was partially digested with Sau3A to generate fragments with an average length of 5Kb. These fragments were ligated in 200 μl to 10 μg BamHI-digested pJDB207. E. coli strain DH1 was transformed with the ligated mixture to generate a "bank" of $5 \times 10^4$ ampicillin-resistant, tetracycline-sensitive clones. Plasmid DNA was prepared from this bank and used to transform S. cerevisiae strain X4003-5B to Leu+. Regeneration agar containing ca. $7 \times 10^4$ Leu+ transformants was homogenised with sterile water in a domestic blender and samples (0.5 ml) were spread onto plates of DEXNB agar. A few strong-growing colonies (ca. 10 to 20 per plate) were obtained after 7 to 9 days at 25° C. and shown to retain a Dex+ Leu+ phenotype when subcultured, whilst remaining auxotrophic for adenine, histidine, methionine, uracil and tryptophan. Plasmid DNA prepared from one of these yeast transformants was used to obtain ampicillin-resistant transformants of DH1, from which miniscale preparation of DNA were digested with E. coRI and analysed by agarose gel electrophoresis. Plasmid pLHD30 (see FIG. 1a), conferred both Leu+ and Dex+ phenotype on X4003-5B by transformation. Restriction analysis revealed pLHD30 to possess both a small (0.9 Kb) and a large (3.6 Kb) insert separated by vector sequences which are oriented in tandem. Such a structure could have arisen during ligation or by intermolecular recombination in vivo. (In FIG. 1, DNA from BRG536 and DNA from pJDB207 are represented by the filled and empty areas respectively. Bm=BamHI, Bg=BglII, E=EcoRI, H=HindIII, K=KpnI, P=PstI, Figures are in Kb).

pLHD301 (see FIG. 1b) was isolated from DH1 after transormation with pLHD30 DNA that had been partially digested by PstI and religated to remove the small insert and one vector sequence. This plasmid retained the ability to confer a Dex+ phenotype on Dex− strains thus showing that a functional DEX gene had been cloned, and is included within a 3.6 Kb insert, which possesses single sites for the restriction enzymes BamHI, BglII, EcoRI, HindIII, KpnI and PstI (see FIG. 1c).

Three separate deletions (labelled A, B and C in FIG. 1c) were made into the cloned fragment using restriction and ligation. Plasmids carrying either deletion A or B failed to confer a Dex+ phenotype on yeast transformants, whereas deletion C did not inactivate DEX. Therefore greater than 1.5 Kb of the insert, extending from the left hand vector-insert junction (see FIG. 1) to an undetermined point between the EcoRI and BglII sites, appears to be essential for DEX expression.

(b) Production of AMG activity by Dex+ transformants

DEX1 strains carrying the CDX1 allele retain AMG activity within the cell wall under conditions of glucose excess, whereas those carrying cdx1 accumulate AMG in the extracellular medium independently of the availability of carbon source (Searle, 1982). dx+ and Cdx− phenotype are readily distinguished by assaying supernatants for AMG activity from mid-log cultures in which excess glucose ( 2.5% w/v) is still present in the culture medium. A comparison of the abilities of BRG536 (cdx1) and BRG205B (CDX1) to produce extracellular AMG, under both excess-glucose and limiting-glucose conditions is given in Table II. With glucose-limited growth, similar amounts of AMG activity were accumulated by both strains. However, under excess glucose conditions, BRG536, but not BRG205B, accumulated extracellular enzyme activity.

The finding that strains X4003-5B and AH22 are genotypically cdx1 and CDX1 respectively (see Table I) provided the opportunity to examine the effects of the CDX1 gene on production of AMG in Dex+ transformants. Three transformants were examined and all produced more (up to 5×) AMG activity than BRG536. Data representative of those obtained are given in Table II. Surprisingly, the presence of the CDX1 allele did not block production of extracellular AMG by transformants of AH22 under conditions of glucose excess. Given that the cloned DEX gene is DEX1, this result means that either (i) amplification of DEX1 expression, by cloning the gene on a multicopy vector, overcomes the regulatory effect of CDX1 or (ii) regulatory or structural regions of DEX1 required for CDX1 regulation, have been excised during cloning.

Although regulation of AMG production by CDX1 was not apparent in Dex+ transformants, these strains did show a substantial increase in specific yield of AMG activity when grown under glucose-limited conditions. It is not known whether this effect, which is also seen with BRG536, is a specific glucose effect, or a consequence of much slower growth rates under limiting-glucose conditions (Table II).

Previous studies on dextrin-fermenting strains have indicated that active AMG is not found intracytoplasmically but is distributed between the cell wall and the external medium (Searle and Tubb, 1981a; Searle, 1982). Therefore, it was of interest to examine the effect of amplified production of AMG on the distribution of activity in CDX1 and cdx1 transformants. From Table III, it can be seen that all three of the Dex+ transformants examined released proportionally more of their AMG activity to the culture medium than BRG536. AH22 transformants, which carry CDX1 and therefore might be expected to retain more AMG activity in the cell wall, were particularly adept in accumulating AMG extracellularly. In contrast to BRG536, some AMG activity was detectable in the "cytoplasmic" fractions from Dex+ transformants (Table III).

c) Identification and characterisation of AMG produced by a Dex+ transformant

The AMG produced by AH22 [transformed with plasmid pLHD30] with that of BRG536 (DEX1) were compared. Extracellular proteins were concentrated by ultrafiltration and analysed by DEAE-Sepharose ion-exchange chromatography and by SDS-PAGE. The bulk of AMG activity from both AH22 [pLHD30] and BRG536 coincided with the first protein peak eluted from the DEAE-Sepharose (see FIG. 2 in which the solid line represents absorbance at 280 nm and the broken line represents AMG activity). This peak (and associated activity) was absent in AH22 [pJDB207] which lacks the cloned DEX gene.

TABLE II

Production of Extracellular Amyloglucosidase by Strains of S. cerevisiae

| | AMG activity (nmol glucose from maltotriose [mg dry cell wt]$^{-1}$ min$^{-1}$ in supernatants from culture with: | |
|---|---|---|
| Strain/Transformant[a] | Excess glucose[b] | Limiting glucose[c] |
| BRG536 | 0.29 | 2.1 |
| BRG205B | 0[d] | 1.9 |
| X4003-5B | 0 | 0 |
| AH22 | 0 | 0 |
| X4003-5B [pJDB207] | 0 | 0 |
| AH22 [pJDB207] | 0 | 0 |
| X4003-5B [pLHD30] | 0.74 | 2.6 |
| AH22 [pLHD30] | 1.4 | 7.3 |
| AH22 [pLHD301] | 1.6 | 6.8 |

[a]With all transformants, the proportion of plasmid-zero cells(Leu$^-$ segregants) was below 5% during growth on selective medium (GYNB, no leucine added). At assay, after growth in non-selective conditions for up to 20 generations, 90% or more of the population retained a Leu$^-$ phenotype.
[b]Cultures assayed after 18 h growth at which time glucoe was still present in the culture medium (ca. 3%, w/v).
[c]Cultures assayed after ca. 40 h growth, at which time the cell density was similar to that of the 18 h excess glucose culture.
[d]0 indicates not detected (i.e. < 0.05 activity units).

TABLE III

Distribution of AMG Activity in Dex+ strains[a]

| | Proportion of AMG (% of total)[b] present as: | | |
|---|---|---|---|
| Strain | Extracellular (culture supernatant) | Cellular (cell homogenate) | Cytoplasmic (protoplast lysate)[c] |
| X4003-5B [pLHD30] | 66 | 34 | 11 |
| AH22 [pLHD30] | 79 | 21 | 4 |
| AH22 [pLHD301] | 79 | 21 | 5 |
| BRG536 | 58 | 42 | 0 |

[a]Strains were grown under conditions of glucose excess and assayed for AMG activity after 18 h (see Table II).
[b]Total activity was derived by summing the activities of the culture supernatant and the corresponding cell homogenate.
[c]Cell membrane fragments were retained in this fraction during assay.

Analysis by SDS-PAGE of pooled fractions containing AMG activity revealed a major high molecular weight band in both AH22 [pLHD30] and BRG536. This band, which was absent in equivalent fractions of AH22 [pJDB207], stained strongly for carbohydrate indicating that it was a glycoprotein. Confirmation that this band did indeed represent AMG was obtained by further purifying the preparation from AH22 [pLHD30]. After chromatofocussing and gel permeation chromatography, a 27-fold purification of AMG activity was achieved in a recovery of 11.5% of total initial activity. This preparation, which analysed for protein:carbohydrate in the ratio 1:2.2, was judged homogeneous by SDS-PAGE, giving only a single band. Since AMG from AH22 [pLHD30] eluted from Biogel P-150 just after the void volume, the molecular size of the enzyme is about 150 Kd. The dex+ transformant, AH22 [pLHD30], produces an AMG of similar molecular size to that produced by BRG536. Further similarities in the enzymes produced by the two strains were apparent when the effects of temperature and pH on AMG activity were examined (FIG. 3a and 3b: see also Table IV). Both enzymes were heat stable up to ca. 45°, were inactivated in parallel at higher temperatures (Table IV) and showed the same optimum pH (5.0) for activity (FIG. 3b). Initial rates of activity over the temperature range 0° to 70° C. were similar, with a maximum at 55° C. (FIG. 3a). (□=AH22 [pLHD30], purified AMG, 16.6 units activity [mg protein]$^{-1}$: O=BRG536, pooled fractions 22–28 after ion-exchange chromatography 5.2 units AMG activity [mg protein]$^{-1}$)

TABLE IV

Temperature inactivation of an amyloglucosidase from AH22 [pLHD30] and BRG536.

| | % Initial activity remaining after 1 h | |
|---|---|---|
| Temperature °C. | AH22 [pLHD30] | BRG536 |
| 25 | 100 | 100 |
| 35 | 100 | 100 |
| 45 | 94 | 97 |
| 55 | 22 | 23 |
| 70 | 0 | 0 | d) Use of DEX as a selectable marker in yeast transformation

Dex+ transformants of X4003-5B and wild-type strains with plasmids pLHD30 and pLHD301 were obtained by allowing plasmid-treated sphaeroplasts to regenerate in a complete medium before imposing the selection for Dex+ (Table V). To impose a selection for dex+, $10^9$ sphaeroplasts which had been treated with plasmid DNA, were inoculated into molten YPG (20 ml) containing sorbitol. After 48 h at 25° C. regeneration agar containing 2 to $5 \times 10^4$ micro-colonies was blended with water and samples ($10 \times 0.5$ ml) spread onto DEXYNE agar. After 7–9 days Dex+ colonies appeared, surrounded by zones of cross feeding: up to 10 colonies were isolated on each plate. No Dex+ colonies were obtained in the absence of plasmid DNA. Using this procedure the overall yield of transformants was substantially reduced when compared with a selection for Leu+ during regeneration (see results obtained with X4003-5B in Table V).

e) DNA sequence of cloned fragment and identification of amino acid sequence of AMG precursor, mature AMG and AMG leader sequence The nucleotide sequence of cloned 3.6 kb fragment from BRG536 was determined and is shown for nucleotides 21 to 2773 in FIG. 4. This sequence contains an open reading frame corresponding to the upper of the three amino acid sequences shown in FIG. 4 and terminating with the TAG stop codon at nucleotides 2562–2564.

The N terminal amino acid sequence determined for mature AMG obtained from S. cerevisiae transformed with a plasmid (pMA91) containing the cloned fragment is identical with the sequence in this reading frame which commences with the phenylalanine corresponding to the TTT codon at nucleotides 207-209.

TABLE V

Transformation of S. cerevisiae strains using DEX plasmids

| Recipient strain | Plasmid | Selection | Transformants recovered (colonies/μg DNA) |
|---|---|---|---|
| X4003-5B | pJDB207 | Leu+ | ca. 10,000 |
| X4003-5B | pLHD30 | Leu+ | ca. 10,000 |
|  |  | Dex+ | 860 |
| X4003-5B | pLHD301 | Leu+ | ca. 5,000 |
|  |  | Dex+ | 750 |
| BRG136D | pLHD30 | Dex+ | 1,100 |
|  | pLHD301 | Dex+ | 860 |
| BRG139A | pLHD30 | Dex+ | 85 |
|  | pLHD301 | Dex+ | 65 |
| BRG401A | pLHD30 | Dex+ | 540 |
|  | pLHD301 | Dex+ | 430 |

On the basis of the DNA sequence alone, however, it is not clear at which point the leader sequence for the AMG starts. There are two methionine residues (M) in this reading frame corresponding to the ATG codons at nucleotides 111-113 and 144-146 which precede this phenylalanine. In order to determine which of these methionine residues corresponds to the start of the AMG leader sequence, the inserted plasmid DNA from a pMA91 was cleaved at the unique Stu 1 site at nucleotide 116 and the resultant DNA reconstructed into pMA91, the resultant plasmid including the sequence from nucleotide 116 to nucleotide 2564 but lacking the ATG codon corresponding to nucleotides 111-113. This resultant plasmid was used to transform S. cerevisiae which was shown to produce AMG in the same way as S. cerevisiae transformed with previous plasmids containing nucleotides 111-113. This shows that the AMG leader sequence commences with the methionine residue corresponding to the ATG at nucleotides 144-146 and identifies the 22 amino acid sequence of the AMG leader peptide.

The experiments detailed above describe the cloning of a gene (DEX) which can be used to confer production of extracellular amylo-α-1, 4-glucosidase on Dex− strains of Saccharomyces cerevisiae. The DEX gene is shown to provide a selectable marker for plasmid transfer into wild-type strains. The use of a DEX gene, either by itself or in conjunction with the use of plasmids carrying the yeast CUP1 gene as a selectable marker (Henderson, 1983), can now be evaluated in the construction of amylolytic strains of yeast for brewing.

Dex+ transformants show amplification of AMG production, which is an expected consequence of cloning a gene on a multicopy vector (Lacroute et al, 1981). However, regulation of AMG production was observed when transformants grown with excess glucose were compared with those grown under glucose limitation. The specific yield of enzyme activity was 3 to 7-fold higher under the latter conditions. This is consistent with the observation of Carlson and Botstein (1982) that glucose regulation of SUC2 is conserved when the gene is maintained on a multicopy plasmid.

In AH22 transformants under conditions of glucose excess, some influence of the CDX1 gene was expected on accumulation of AMG in the extracellular medium. However, release of enzyme was not blocked under these conditions and only a small proportion of total activity was retained within the cell wall. Since the possibility that Dex+ transformants produce a substantially altered (e.g. smaller) AMG has been ruled out (see above), the lack of influence of CDX1 in this case suggests that its regulatory effect in DEX1 strains such as BRG205B, is exerted not at the level of the cell wall, but at an earlier stage in AMG synthesis. For example, if CDX1 confers a step-down in production of AMG-specific mRNA, the effect could be overcome either by gene amplification or by excision of regulatory non-coding regions during cloning.

Finally, a northern blot analysis of the RNA transcribed from strain AH22 (LEU2−, HIS3−) transformed with pLHD301 was performed. The RNA from pMA91-DEX, (see FIG. 9 of the accompanying drawings) a plasmid in which the expression of the DEX gene is under the control of the efficient PGK promoter was compared to that from pLHD301. Both plasmids are present at about 100 copies per cell. (Plasmid pMA91—also known as pM3013—is described in published European patent application EP-A2-0073653). To construct pMA91-DEX, the Stu1 site, just downstream from the first identified ATG in the DEX open reading frame was converted to a BglII site and the fragment inserted into the unique BglII expression site in pMA91. pLHD301 has about 100 bp of the 5' non-coding region of the DEX gene. Both plasmids were transformed into AH22 and grown on either a glucose or dextrin carbon source. The RNA from pMA91-DEX is about 30 fold more abundant than that from pLHD301 on the dextrin source and about 50 fold more when grown on glucose. Thus the 100 bp of 5' non-coding region on the DEX gene is not a good promoter. The levels of RNA from pLHD301 in either a dextrin or a glucose carbon source are similar to the chromosomal PGK transcript, present as about 1% if mRNA transcribed from a single-copy gene. The fact that the RNA levels are similar regardless of the carbon source also suggests that the sequences which permit regulation of DEX transcription are not present in this plasmid. The RNA is of the expected size (2.5 Kb) and is present as about 1% of the mRNA population in yeast (data not shown).

The position at which the RNA in pLHD301 initiates was mapped by primer extension using a synthetic oligonucleotide. The 20 bp primer was holmogolous to a region just after the second ATG. The sizes of the extended products suggest that there are two start sites, 20 and 28 bp upstream from the second ATG. Both RNAs initiated on an A. The positions of the start sites are located in favourable positions relative to the potential TATA box located about 70 bp upstream from the second ATG. It is probable that the second ATG apparent in the DNA sequence is used as the translation initiation condon, since it is the first ATG present on the transcripts.

The DEX gene contains a yeast consensus splicing signal, TACTAAC about 1 Kb from the ATG. There are no good matches to the consensus splice donor or acceptor sites. It was possible that the DEX gene contained an intron which would be removed by splicing the RNA transcript. An $S_1$ protection experiment, set up to test this, suggested that the gene does not contain an intron. The protected fragment was about 2.5 Kb. If the RNA was spliced then two protected fragments of 1.0 Kb or less and 1.4 Kb or less would be expected, since the TACTAAC sequence would be located in the intron. Even at high concentration of $S_1$ nuclease no smaller fragments could be detected. The control experiment in which a DNA molecule which differed from an RNA transcript by 5 bp mismatch in the centre of the RNA shows that the $S_1$ nuclease recognises this mismatch. Therefore, the splicing of an intron from the DEX RNA would most likely be detected in this experiment.

The RNA transcribed from the DEX gene in pLHD301 is present at about 1% of mRNA in yeast and is not spliced. There are two RNA initiation sites located 20 and 28 bp upstream from the second ATG (identified from the DNA sequence). The RNA start sites are preceded by a TATA box located 70 bp upstream from the second ATG. This ATG is present at the start of a potential leader peptide of 20 amino acids. This sequence has been engineered into pMA91 to examine whether it can direct the secretion from yeast of a human gastric lipase or interferon gene.

It has been shown that a brewing strain of S. cerevisiae (NCYC1324), transformed with a vector including the DEX gene, and thus capable of producing extracellular AMG, when used in brewing trials, produces a beer with a lower specific gravity than would be expected with untransformed cells of the same strain of yeast.

EXAMPLE 2

To demonstrate that the DEX gene can be used to direct the secretion of heterologous proteins from S. cerevisiae, an in phase translational fusion was made between the 5' end of the DEX gene and the intact met-human gastric lipase (hGL) gene.

The cloning and expression of the hGL is described in copending International patent application PCT/GB 85/00364.

A gene encoding human gastric lipase was isolated from a cDNA clone bank made from mRNA prepared from a sample of human stomach tissue. Human gastric lipaseclones were identified by homology with a cDNA clone of rat lingual lipase previously obtained as described in published European patent application EP-A1-0131418. (The disclosures of which are incorporated herein by reference). A freshly obtained section of human stomach wall tissue approximately 2 cm wide was stored in liquid nitrogen. The section contained complete mucosal, muscle and serosa layers. mRNA was prepared by guanidinium isothiocyanate extraction of the frozen ground complete tissue (Maniatis et al (1982) "Molecular Cloning—A Laboratory Manual". Cold Spring Harbor Laboratory). Polyadenylated RNA was isolated from this by oligo-dT cellulose chromatography (Harris, T. J. R. et al (1975) J. Gen. Virol 29 299-312).

The presence of an mRNA species encoding an acid stable lipase was suggested by Northern Blot analysis (Thomas, P. S. (1980) PNAS USA, 77 5201-5205). By this technique polyadenylated stomach RNA was separated on the basis of molecular weight by gel electrophoresis and probed with a cDNA clone of the rat lingual lipase gene labelled by nick translation (Rigby, P. W. J. et al J. Mol. Biol. 113, 237-251). This labelled gene specifically hybridised with a mRNA species with an apparent size of approximately 1500 bases. This mRNA species was of a size capable of encoding a protein of the apparent size of human gastric lipase together with untranslated 5' and 3' sequences of such a message.

cDNA was prepared to the human stomach mRNA. First strands were synthesised by poly(dT) priming and elongation by AMV reverse transcriptase (Retzel, E. F. et al (1980) Biochemistry 19 513-518). Second strands were synthesised by the action of RNase H, E. coli DNA polymerase I and E. coli DNA ligase as described (Gubler, V. and Hoffman, B. (1983) Gene 25 263-269). The double stranded cDNA was tailed at the 3' ends with poly(dT) (Villa-Komaroff et al (1978) PNAS USA, 75:3727). Tailed fragments were annealed into pBR322 which had been cleaved and poly(dG) tailed at the PstI site. These hybrids were transformed into E. coli DH1 competent for transformation (Maniatis et al (1982) "Molecular Cloning—A Laboratory Manual". Cold Spring Harbor Laboratory). The transformants were screened by colony hybridisation on nitrocellulose filters (Hanahan, D. and Melson, M. (1980) Gene 10 63-67). The hybridisation probe was the DNA fragment containing the coding region for rat lingual lipase labelled by nick translation (Rigby, P. W. J. et al (1977) J. Mol. Biol. 113 237-252).

Putative human gastric lipase clones were mapped for restriction endonuclease cleavage sites and subjected to DNA sequencing (Sanger, A. J. H. (1980) "Methods in Enzymology", Academic Press 65 560-580) using a synthetic single-stranded oligodeoxyribonucleotide primer which hybridised to a region just 3' to the cloned segment. Clones were shown to encode the lipase by sequence homology with the rat lingual lipase cDNA sequence and comparison of the predicted sequence from the cDNA clones with the N-terminal amino acid sequence of native human gastric lipase isolated from stomach aspirate FIG. 5. One clone was identified (pGL17), approximately 1450 bp long containing the entire coding sequence for the gastric prelipase. The 5' end of the clone was shown to be within 20 nucleotides of 5' terminal nucleotide of the message. This was demonstrated by the sequence obtained from the primer extension. In this technique a synthetic oligodeoxyribonucleotide primer was hybridised specifically to a region of the human gastric lipase mRNA encoding the N-terminal protein sequence. This primer was extended to the 5' end of the mRNA and the sequence determined (FIG. 5).

The DNA sequence of the coding strand of the pre human gastric lipase gene is shown in FIG. 5. Numbers below the DNA sequence represent the base number. Base 1 is the first nucleotide of the cloned human gastric lipase sequence in pGL17. An "*" indicates the stop codon TAG which is followed by a 3' untranslated region. Underlined letters above the derived amino acid sequence represent the N-terminal amino acid sequence obtained directly from purified human gastric lipase. Spaces in the directly obtained amino sequence represent undetermined amino acids. Amino acids −19 to −1 represent a putative signal sequence and +1 to 379, the amino acid sequence of the mature gene. Broken underlining indicates the potential glycosylation sequence.

Plasmid vectors for the expression of methionine human gastric lipase were constructed based on plasmid pMA91 (also known by the designation pMA3013) as described in the published European patent application EP-A2-0073653. These vectors contain the yeast phosphoglycerate kinase (PGK) promoter and the PGK gene 3' end flanking sequences sandwiching the methionine-human gastric lipase gene. A plasmid pMB1 (not shown) was constructed by insertion of BglII fragment containing the entire pre human gastric lipase gene. The plasmid pYC3 (FIG. 6) was constructed by removal of a BglII to AccI fragment from pMB1 containing the 3' end of the lipase gene and ligated to the BglII and AccI fragment of the 5' end of the gene obtained from pCML1 (described above). This was inserted into the BglII site of pMA3013 to form pYC3. The plasmid pYC3 was transformed into the diploid strain MD50 and the haploid MD40/4C and transformants grown up in nitrogen based medium as described in the published European patent application EP-A2-0073653.

Plasmid pMA91-DEX (the construction of which is described in Example 1) was digested under standard conditions with BamHI restriction enzyme. The small BamHI fragment carrying most of the DEX structural gene, was replaced by two DNA fragments isolated from pYC3. These fragments were a BalII-AccI DNA fragment, comprising the 5' end of the hGL gene, and an AccI-BamHI DNA fragment comprising the 3' end of the hGL gene, and the pGK transcriptional terminator, and were isolated by the method of Vogelstein & Guillespie (Proc. Natl. Acad. Sci USA 76 (1979) 615–619. The purified DNA fragments were ligated together under standard conditions, and transformed into E. coli DH1.

The fusion junction was as follows:

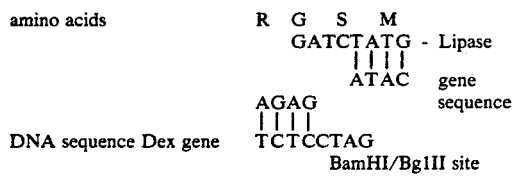

Plasmid DNA was isolated from transformants and analysed by restriction digestion, one plasmid comprising the correct DNA fragments was designated pMA91DexhGL.

Figure 7A:
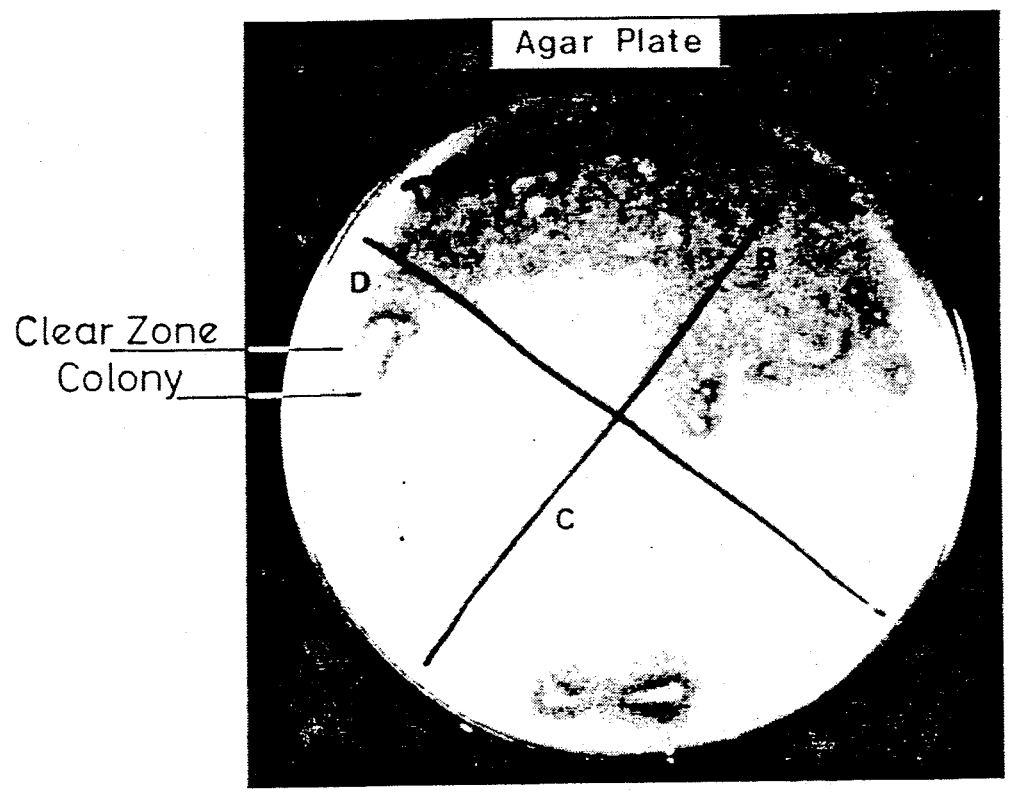
Figure 7B:
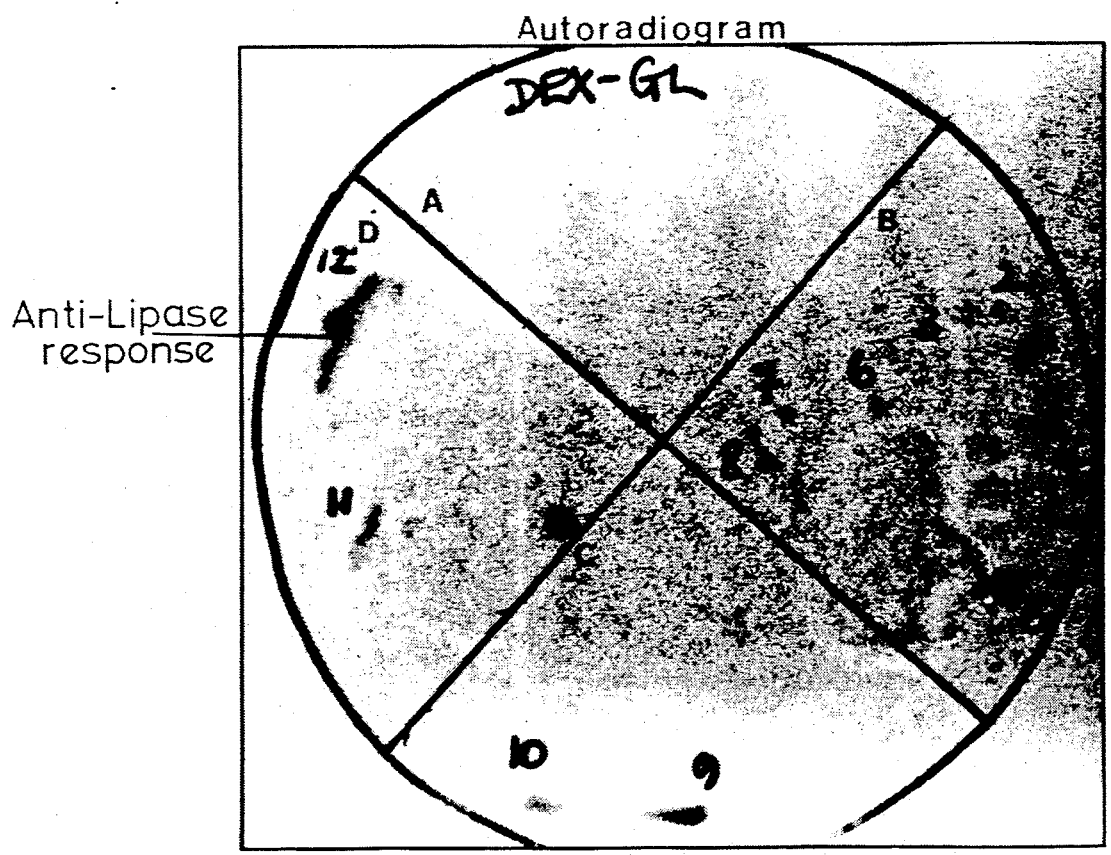

Plasmid pMA91DexhGL was transformed in S. cerevisiae strain MD404C, and the synthesis and secretion of hGL was analysed by (1), an agar plate activity assay, and antibody reaction, and (2), radioactive assay of hGL activity. MD404C pMA91DexhGL, was plated onto yeast nitrogen base minimal plates containing the lipid tributyrin (0.75%), and zones of clearing around colonies, caused by lipase action on the tributyrin emulsion, were detected (FIG. 7a). The plates comprising zones of clearing were analysed for hGL protein, by overlaying with a nitro cellulose filter for 2 hours. The filter was then treated as described for Western Blots (Towbin, H., et al (1979), "Electrophoretic Transfer of Proteins from Polyacrylamide Gels to Introcellulose Sheets: Procedure and some applications, PNAS" 76: 4350–4353) using a polyclonal antibody to hGL, and iodinated protein A (FIG. 7b). After washing, the filter was analysed by autoradiography, and immunoreactive material was detected, within the zones of clearing.

MD404C pMA91DexhGL was grown in liquid culture (100 ml) at 30° C., in yeast nitrogen base minimal medium. The cells were harvested by centrifugation, and the medium fraction filtered through sterile filters. The cell pellet was divided into two halves, one was resuspended in 10 nM Tris. HCl(pH7.5) buffer, and broken in a French pressure cell, to give total cell extracts. The other half of the pellet was subjected to lyticase treatment (J. H. Scott & R. Schekman J. Bact. 142 414-423, (1980) to generate cell wall, and cell cytoplasm fractions. These fractions were analysed for lipase activity as follows:

Stock Solutions

1. Label: 15μmoles phosphatidyl choline, 5 mCi $^3$H-triolein, 200μmoles cold triolein and 3.3 ml anhydrous glycerol were sonicated for 2 periods of 1 min. on setting 7.
2. Cold emulsion as for 1 above without label.
3. Reaction buffer: 0.1M $Na_2HPO_4$ adjusted to ph5.4 with 0.1M citric acid.
4. Extraction buffer: 0.2M Glycine/NaOH pH12.5.
5. Extraction solvent: Methanol: Chloroform: Hexane (1.41:1.25:1).

Method

1. Prepare a 7% w/v solution of defatted BSA in the reaction buffer.
2. Prepare a dilution of label in cold emulsion : one in ten is suitable.
3. Add together equal quantities of the above two and sonicate to give a fresh substrate preparation. (Setting 7, 50% pulsed for 2×1 minute periods on ice).
4. Aliquot 50μl of substrate and 25 μl BSA buffer per tube.
5. Equilibrate tubes at 37° C. for 30 mins.
6. Add 25μl of lipase (dilutions in citrate buffer). Mix thoroughly.
7. Incubate with shaking 30 mins.
8. Add 1.625 ml of extraction solvent to stop reaction and 0.525 ml of alkaline buffer. Vortex vigorously.
9. Centrifuge to separate phases : 2000 RPM, 25° C., 15 mins. IEC Centra.
10. Count 0.5 ml aliquots of the aqueous phase in 3.5 ml Beckman Redisolve.

The results are shown in Table VI below:

TABLE VI

| Fraction | % Total Lipase Activity | mg/L* hGLipase |
| --- | --- | --- |
| Media | 11 | 0.7 |
| Cell Wall | 21 | 1.3 |
| Intra Cellular | 68 | 4.2 |
| Total Cellular | 100 | 5.2 |

*These values were estimated using hGLipase enzyme standard.

Gastric lipase activity was detected in all the cell fractions assayed; approximately 32% of all the activity was extracellular (cell wall or medium) whilst 67% was intracellular. These results demonstrate that the 5' region of the DEX gene directs heterologous proteins to the medium and cell wall. Md404C carrying pYC3, a plasmid expressing met hGL, was used as a control, and only showed lipase activity in the intracellular fraction.

The protein product of the human gastric lipase—Dextrinase gene fusion was further analysed using Western blot analysis of 10% polyacrylamide—SDS gels (Towbin, H., et al (1979)). The results of such a blot are shown in FIG. 8. Track 1 is the pattern of bands observed with a cell extract made from S. cerevisiae MD50 carrying pYC3 (FIG. 6), the major immunoreactive band was the size expected for mature human gastric lipase (plus an additional methionine residue). Tracks 2, 3 and 4 are the pattern of bands observed with a cell extract made from MD50 carrying pMA91-DexhGL. There is one protein band corresponding in size to the mature hGL protein, this suggests that the fusion protein signal has been cleaved off. This process is indicative of entry into the endoplasmic reticulum and the є-cretory process. Above this band there are at least 4 other bands of immunoreactivity, which are not found intrack 1, these bands are typical of protein glycosylation and secretion, and hGL is naturally glycosylated during secretion. These results therefore, provide further evidence that the dextrinase leader sequence is capable of directing heterologous proteins into the secretory process.

EXAMPLE 3

An experiment was conducted to show that a DNA sequence containing the signal sequence of the yeast DEX gene (encoding amylo-α-1,4-glucosidase) can direct secretion of human interferon α-2 from yeast cells into the culture medium.

The plasmid used for these experiments was constructed by replacing the DEX coding region in pMA91-DEX with a 940 bp BamHI fragment containing the human interferon-α-2 (IFN) gene. This gave plasmid pMA91-DEX-IFN, in which 110 bp of the 5' region of DEX containing the signal sequence is linked to the IFN gene (FIG. 9). In this plasmid, the hybrid DEX-IFN gene is under the control of the PGK promoter. pMA301-1 which contains the IFN gene also under control of the PGK promoter (Mellor et al, (1985), Gene, 33, 215-226) was used as a control in these experiments.

The yeast strain MD40/4c (ura2, trpl, leu2.3, leu2.12, his3.11, his3.15) was transformed with pMA91-DEX-IFN and pMA301-1 to produce transformants T91-DEX-IFN and T301-1 respectively. T91DEX-IFN and T301-1 were grown overnight at 30° C. in synthetic complete medium without leucine (SC: 0.67% yeast extract without amino acids, 1% glucose) to a cell density of $4 \times 10^6$ cells/ml. The cells were harvested and soluble protein extracts were prepared as described by Mellor et all (1983, Gene. 24, 1-14). The protein extracts were analysed for the presence of IFN by Western blotting procedures using a monoclonal antibody from cell-line NK2 (Celltech Ltd.) as a probe. Cell extracts T91-DEX-IFN produced a polypeptide which had the mobility of authentic IFN as compared with T301-1 extracts and also a polypeptide of higher molecular weight which is thought to be a DEX-IFN fusion protein (data not shown).

To determine whether the DEX signal sequence could direct secretion of IFN into the culture medium, T91-DEX-IFN and T301-1 were grown at 30° C. overnight in SC without leucine to a density of $3 \times 10^7$ cells/ml (early stationary phase). 150 ml of each culture were centrifugated at 3K for 5 min. and the media supernatants, to which 1 mM PMSF (Sigma) was added, were dialysed against STE (10 mM NaCl; 10 mM Tris pH7.5; 1 mM EDTA) for 4 days. The supernatant volumes were reduced by dialysing against PEG 4000 (Sigma) for approximately 2 hrs. followed by further dialysis against STE for 3 days. The supernatants were dried down in a Speed Vac Concentrator (Savant Instruments Inc.) and resuspended in a total volume of 400μl sterile water (AR grade). The samples were divided into two portions and both aliquots were assayed in parallel for IFN activity using an IRMA assay (supplied by Celltech Ltd.). The results are shown in Table VII.

TABLE VII

| Assay for IFN Activity in Media Supernatants | | |
|---|---|---|
| IFN Standards | cpm | |
| Units/200 μl | Sample 1 | Sample 2 |
| 1000 | 3111 | 3143 |
| 500 | 2083 | 2305 |
| 250 | 1022 | 921 |
| 100 | 502 | 561 |
| 50 | 334 | 258 |
| 25 | 180 | 163 |
| 12.5 | 104 | 127 |
| 0 | 60 | 59 |

TABLE VII-continued

| Assay for IFN Activity in Media Supernatants | | |
|---|---|---|
| | cpm | |
| Media Supernatants | Sample 1 | Sample 2 | [IFN] Units/sample |
| T301-1 undiluted | 76 | 68 | 19 |
| 1/10 diluted | 63 | 62 | 0 |
| T91-DEX-IFN undiluted | 3736 | 3707 | 1000 u |
| 1/10 diluted | 1863 | 2242 | 468 |

IFN was detected in the undiluted (off scale 1000 u) and the 1/10 diluted sampled (mean=468u) of media from T91-DEX-IFN. Very small amounts of IFN (mean=-19u) were detected in undiluted media samples from T301-1. Extrapolation of the IFN activity in diluted samples of media from T91-DEX-IFN gives a total IFN activity of $9.36 \times 10^3$ units from 150 ml culture; this is equivalent to 46.8 ng IFN.

These results show that the DEX signal sequence can direct secretion of a heterologous gene product into the culture medium. The conditions for secretion could be optimised using yeast strains whose genetic backgrounds may be more compatible with secretion of the homologous DEX product than that of MD40/4c. Similarly, experiments need to be carried out to define the optimum growth conditions for most efficient secretion.

It will be understood that the invention is described by way of Example only and modifications of detail may be made within the scope of the invention.

Anon: E.B.C. Analytica Microbiologica. J. Inst. Brew. 83 (1977) 109-118.

Beggs, J. D.: Transformation of yeast by a replicating hybrid plasmid. Nature 275 (1978) 104-109.

Beggs, J. D.: Multiple-copy yeast plasmid vectors, in von Wettstein, D., Stenderup, A., Kielland-Brandt, M., and Friis, J. (Eds.), Molecular Genetics in Yeast, Alfred Benzon Symposium, Vol. 16. Munksgaard, Copenhagen, 1981, pp. 383-395.

ten Berge, A. M. A., Zoutewelle, G. and van de Poll, K. W.: Regulation of maltose fermentation in *Saccharomyces carlsbergensis*. The function of the gene MAL6 as recognised by mal6 mutants. Mol. Gen. Genet. 123 (1973) 233-246.

Bolivar, F. and Backman, K.: Plasmids of *Escherichia coli* as cloning vectors. in Wu, R. (Ed.), Recombinant DNA, Methods in Enzymology, Vol. 68 Academic Press, New York, 1979, pp. 245-267.

Brown, A. J. P., Goodey, A. R. and Tubb, R. S.: Interstrain transfer of the 2μm DNA plasmid of Saccharomyces by cytoduction. J. Inst. Brew. 87 (1981) 234-238.

Carlson, M. and Botstein, D.: Two differentially regulated mRNAs with different 5' ends encode secreted and intracellular forms of yeast invertase. Cell 28 1982) 145-154.

Clancy, M. J., Smith, L. M. and Magee, P. T.: Developmental regulation of a sporulation-specific enzyme activity in *Saccharomyces cerevisiae*. Mol. Cell. Biol. 2 (1982) 171-178.

Colonna, W. J. and Magee, P. T.: Glycogenolytic enzymes in sporulating yeast. J. Bact. 134 (1978) 844-853.

Erratt, J. A. and Stewart, G. G.: Genetic and Biochemical studies on yeast strains able to utilise dextrins. J. Amer. Soc. Brew. Chem. 36 (1978) 151-161.

Eveleigh, D.: The microbiological production of industrial chemicals. Sci. Amer. 245 (1981) 130-130.

Fogarty, W. M.: Some recent developments in starch-degrading enzymes, in Priest, F. G. and Campbell, I. (Eds.), Current Developments in Malting, Brewing and Distilling, Proceedings of the IOB Aviemore Conference, Institute of Brewing, London, (1983), 83-110.

Goodey, A. R. and Bevan, E. A.: Production and analysis of yeast hybrids. Curr. Genet. 69 (1983) 69-72.

Goodey, A. R. and Tubb, R. S.: Genetic and Biochemical analysis of the ability of *Saccharomyces cerevisiae* to decarboxylate cinnamic acids. J. Gen. Microbiol. 128 (1982) 2615-2620.

Henderson, R. C. A.: The genetics and applications of copper resistance in yeast, D. Phil. Thesis, University of Oxford, 1983.

Hinnen, A., Meyhack, B. and Tsapis, R.: High expression and secretion of foreign proteins in yeast, in Korhola, M. and Vaisanen, E. (Eds.), Gene Expression in Yeast, Proceedings of the Alko Symposium. Foundation for Biotechnical and Industrial Fermentation Research, Helsinki, 1983, 157-163.

Hollenberg, C. P.: Cloning with 2µm DNA vectors and the expression of foreign genes in *Saccharomyces cerevisiae*, in Hofschneider, P. H. and Goebel, W. (Eds.), Gene Cloning in Organisms Other than *E.coli*, Current Topics in Microbiology and Immunology, Vol. 96. Springer-Verlag, Berlin, 1982, 119-144.

Hopkins, R. H.: Analase systems in brewery yeast, in Proceedings of the 5th European Brewing Convention Congress, Baden-Baden, Elsevier, Amsterdam, 1955, 52-64.

Lacroute, F., Bach, M. L., Chevallier, M. R., Hubert, J. C., Losson, R., Botstein, D. and Loison, G.: Transcriptional regulation of the yeast pyrimidine genes, in von Wettstein, D., Stenderup, A., Kielland-Brandt, M. and Friis, J. (Eds.), Molecular Genetics in Yeast, Alfred Benzon Symposium, Vol. 16 Munksgaard, Copenhagen, 1981 175-181.

Laemmli Cleavage of structural proteins during the assembly of the head of bacteriophage T4. Nature 227 (1970) 680-685.

Lowry, O. H., Rosenbrouogh, N. J., Farr, A. L. and Randall, R. J.: Protein measurement with the Folin phenol reagent. J. Biol. Chem. 193 (1951) 265-275.

Maniatis, T., Fritsch, E. F. and Sambrook, J.: Molecular Cloning: A Laboratory Manual, Cold Spring Harbour Laboratory, Cold Spring Harbour, N.Y., 1982.

Messing and Vieira: Gene, 19, 269-276.

Rothstein, S. J., Lazarus, C. M., Smith, W. E., Baulcombe, D. C. and Gatenby, A. A.: Secretion of a wheat α-amylase expressing in yeast. Nature 308 (1984) 662-665.

Sanger et al: PNAS USA, 74, (1977), 5463-5467.

Searle, B. A.: Utilisation of carbohydrates by brewing and amyloytic strains of Saccharomyces. Ph.D. Thesis, Univ. Bath, 1982.

Searle, B. A. and Tubb, R. S.: Regulation of amyloglucosidase production by *Saccharomyces diastaticus* J. Inst. Brew. 87 (1981a) 244-247.

Searle, B. A. and Tubb, R. S.: A rapid method for recognition strains of yeast able to hydrolyse starch or dextrin.FEMS Microbiol. Lett. 11 (1981b) 211-212.

Sherman, F. and Lawrence, C. W.: Saccharomyces, in King, R. C. (Ed.) Handbook of Genetics. Plenum, New York, 1974 359-446.

Southern, E. M.: Detection of specific sequence among DNA fragments separated by gel electrophoresis. J. Mol. Biol. 98 (1975) 503-517.

Stewart, G. G. and Russell, I.: Aspects of the biochemistry and genetics of sugar and carbohydrate uptake by yeasts, in Spencer, J. F. T. Spencer, D. M. and Smith A. R. W. (Eds.), yeast Genetics: Fundamental and Applied Aspects. Springer-Verlag, New York, 1983 461-484.

Tamaki, H.: Purification of glucoamylase isoenzymes produced by *Saccharomyces diastaticus*, Doshisha Joshi Diagaku Gakujutsu Kenkyu Neupo 31 (1980), 270-286.

Tamaki, H.: Genetic studies of ability to ferment starch in Saccharomyces: gene polymorphism. Molec. Gen. Genet. 164 (1978) 205-209.

Thomsen, K. K.: Mouse α-amylase synthesised by *Saccharomyces cerevisiae* is released into the culture medium. Carlsberg Res. Commun. 48 (1983) 545-555.

Tubb, R. S.: Genetic pathways to super-attenuating yeasts, in Priest, F. G. and Campbell, I. (Eds.), Current Developments in Malting, Brewing and Distilling, Proceedings of the 10th Aviemore Conference, Institute of Brewing, London, (1983) 67-82.

Tubb, R. S.: Genetics of ethanol-producing microorganisms, in Stewart, G. G. and Russel, I. (Eds.), CRC Critical Reviews in Biotechnology, Vol. 1, CRC Press, Boca Raton, Florida, (1984) 241-261.

Tubb, R. S., Searle, B. A., Goodey, A. R. and Brown, A. J. P.: Rare mating and transformation for construction of novel brewing yeasts, in Proceedings of the 18th European Brewing Convention Congress, Copenhagen. IRL Press, London, (1981) 487-496.

van der Walt, J. P.: Genus 16. Saccharomyces, Mayenemend, Reess, in Lodder, J. (Ed.), The Yeasts, A Taxonomic Study. North-Holland, Amsterdam, (1970) 555-718.

Webster, T. D. and Dickson, R. C.: Direct selection of *Saccharomyces cerevisiae* resistant to the antibiotic G418 following transformation with a DNA vector carrying the kanamycin-resistance gene of Tn903. Gene 26 (1983) 243-252.

Yamashita, I. and Fukui, S.: Molecular cloning of a glucoamylase producing gene in the yeast Saccharomyces, Agric. Biol. Chem. 47 (1983) 2689-2692.

Yarrow, D.: Genus 22. Saccharomyces Meyen ex Reess, in Kreger-van Fij, N. J. W. (Ed.), The Yeasts, A Taxonomic Study. Elsevier, Amsterdam, (1984) 379-395.

Zacharius, R. M., Zell, T. E., Morrison, J. H. and Woodlock, J. J.: Glycoprotein staining following electrophoresis on acrylamide gels. Anal. Biochem. 30 (1969) 148-152.

I claim:

1. A yeast expression vector comprising a DNA sequence coding for a precursor polypeptide comprising the amino acid sequence:

met-gln-arg-pro-phe-leu-leu-ala-tyr-leu-val-leu-ser-leu-leu-phe-asn-ser-ala-leu-gly-X wherein X comprises a polypeptide;

said DNA sequence being positioned relative to a promoter capable of directing expression of the DNA sequence when the vector is transformed into a yeast host organism, provided that the promoter is not an amylo-α-1,4-glucosidase gene promoter.

2. A yeast expression vector according to claim 1 wherein the promoter is derived from at least a functionally active portion of the 5' region of the yeast phosphoglycerate kinase gene.

3. A yeast transformed with an expression vector according to claim 1.

4. A brewing strain of yeast transformed with a vector according to claim 1 to 2 wherein the polypeptide X is an amylolytic enzyme.

5. A fermentation process for producing ethanol comprising the step of culturing a yeast as defined in claim 4 in the presence of starch or dextrin.

6. A process for the production of a polypeptide comprising growing in a culture medium a yeast host organism transformed with a vector as defined in claim 1 and isolating the polypeptide from the culture medium.

7. An expression vector according to claim 1 wherein the DNA sequence coding for said precursor polypeptide comprises the nucleotide sequence:

5'-ATGCAAGACCATTTCTACTCGCT-TATTTGGTTCCTTT CGCTTCTATT-TAACTCAGCTTTGGGT($X^1$)-3' wherein $X^1$ comprises a nucleotide sequence coding for polypeptide X.

8. A yeast expression vector according to claim 1 wherein X comprises a human gastric lipase protein.

9. A yeast expression vector according to claim 1 where X comprises interferon-α.

* * * * *